(12) United States Patent
Chen et al.

(10) Patent No.: US 10,905,665 B2
(45) Date of Patent: Feb. 2, 2021

(54) CHEMICAL MODULATORS OF SIGNALING PATHWAYS AND THERAPEUTIC USE

(71) Applicant: Duke University, Durham, NC (US)

(72) Inventors: Wei Chen, Chapel Hill, NC (US); Robert A. Mook, Jr., Chapel Hill, NC (US); Jiangbo Wang, Durham, NC (US); Xiu-rong Ren, Durham, NC (US); Minyong Chen, Durham, NC (US); Lawrence S. Barak, Durham, NC (US); Herbert Kim Lyerly, Chapel Hill, NC (US); David Needham, Durham, NC (US)

(73) Assignee: Duke University, Durham, NC (US)

( * ) Notice: Subject to any disclaimer, the term of this patent is extended or adjusted under 35 U.S.C. 154(b) by 445 days.

(21) Appl. No.: 15/739,390

(22) PCT Filed: Jun. 24, 2016

(86) PCT No.: PCT/US2016/039295
§ 371 (c)(1),
(2) Date: Dec. 22, 2017

(87) PCT Pub. No.: WO2016/210289
PCT Pub. Date: Dec. 29, 2016

(65) Prior Publication Data
US 2020/0038350 A1 Feb. 6, 2020

Related U.S. Application Data

(60) Provisional application No. 62/184,133, filed on Jun. 24, 2015, provisional application No. 62/188,131, filed on Jul. 2, 2015, provisional application No. 62/193,935, filed on Jul. 17, 2015.

(51) Int. Cl.
| | | |
|---|---|---|
| *A61K 31/167* | (2006.01) | |
| *A61P 1/16* | (2006.01) | |
| *A61P 35/00* | (2006.01) | |
| *A61K 9/00* | (2006.01) | |
| *A61K 31/18* | (2006.01) | |
| *A61K 31/196* | (2006.01) | |
| *A61K 31/4015* | (2006.01) | |
| *A61K 31/4188* | (2006.01) | |
| *A61K 31/47* | (2006.01) | |
| *A61K 31/536* | (2006.01) | |
| *A61K 31/5375* | (2006.01) | |

(52) U.S. Cl.
CPC .......... *A61K 31/167* (2013.01); *A61K 9/0053* (2013.01); *A61K 31/18* (2013.01); *A61K 31/196* (2013.01); *A61K 31/4015* (2013.01); *A61K 31/4188* (2013.01); *A61K 31/47* (2013.01); *A61K 31/536* (2013.01); *A61K 31/5375* (2013.01); *A61P 1/16* (2018.01); *A61P 35/00* (2018.01)

(58) Field of Classification Search
CPC .................................................. A61K 31/167
See application file for complete search history.

(56) References Cited

U.S. PATENT DOCUMENTS

| | | |
|---|---|---|
| 2006/0009506 A1 | 1/2006 | Westwick et al. |
| 2009/0048282 A1 | 2/2009 | Hauze et al. |
| 2009/0239919 A1 | 9/2009 | Wood et al. |
| 2010/0041014 A1 | 2/2010 | Hyde et al. |
| 2010/0041133 A1 | 2/2010 | Hyde et al. |
| 2010/0298200 A1 | 11/2010 | Liu et al. |
| 2011/0046133 A1 | 2/2011 | Sung et al. |
| 2011/0300137 A1 | 12/2011 | McKenzie |
| 2012/0082659 A1 | 4/2012 | Land et al. |
| 2012/0114670 A1 | 5/2012 | Land et al. |
| 2012/0134975 A1 | 5/2012 | Hyde et al. |
| 2013/0005802 A1 | 1/2013 | Chen et al. |
| 2013/0121919 A1 | 5/2013 | Feng et al. |
| 2013/0261142 A1 | 10/2013 | Lai |
| 2014/0221411 A1 | 8/2014 | Kim et al. |

FOREIGN PATENT DOCUMENTS

| | | |
|---|---|---|
| CA | 2606658 A1 | 4/2008 |
| CN | 101254183 A | 9/2008 |
| CN | 101775032 A | 1/2009 |
| CN | 102010348 A | 4/2011 |
| EP | 1514544 A1 | 3/2005 |
| EP | 1649852 A1 | 4/2006 |

(Continued)

OTHER PUBLICATIONS

Gaikwad et al., "The Use of Bioisosterism in Drug Design and Molecular Modification," American Journal of PharmTech Research Am., 2012, retrieved from the internet: <http://citeseerx.ist.psu.edu/viewdoc/download?doi=10.1.1.301.520&rep=rep1&type=pdf> 24 pages.
Mook et al., "Structure-activity studies of Wnt/β-catenin inhibition in the Niclosamide chemotype: Identification of derivatives with improved drug exposure," Bioorganic & Medical Chemistry, 2015, 23, 5829-5828.
Toner et al., "The novel toluidine sulphonamide EL102 shows pre-clinical in vitro and in vivo activity against prostate cancer and circumvents MDR1 resistance," British Journal of Cancer, 2013, 109(8): 2131-2141.
Yan et al., "Synthesis, characterization, and evaluation of a novel inhibitor of Wnt/β-catenin signal pathway," Molecular Cancer, 2013, 12(1): 116, 10 pages.

(Continued)

*Primary Examiner* — Svetlana M Ivanova
(74) *Attorney, Agent, or Firm* — Michael Best & Friedrich LLP

(57) ABSTRACT

Described are methods of treating a disease associated with dysregulation of the Wnt/Frizzled signaling pathway. The methods include identifying subjects in need of therapy, administering inhibitors of the Wnt/Frizzled signaling pathway, pharmaceutical compositions including the inhibitors, and methods of using the compounds and compositions for treating cancer, bacterial and viral infection, lupus, type II diabetes, nonalcoholic steatohepatitis (NASH) and nonalcoholic fatty liver disease (NAFLD) in a subject.

2 Claims, 9 Drawing Sheets

(56) References Cited

FOREIGN PATENT DOCUMENTS

| | | |
|---|---|---|
| GB | 2488028 A | 8/2012 |
| RU | 2370222 C2 | 10/2009 |
| WO | WO 2003/103665 A1 | 12/2003 |
| WO | WO 2004/006906 A2 | 1/2004 |
| WO | WO 2005/007151 A1 | 1/2005 |
| WO | WO 2005/060951 A2 | 7/2005 |
| WO | WO 2006/036737 A2 | 4/2006 |
| WO | WO 2006/122007 A1 | 11/2006 |
| WO | WO 2008/027912 A2 | 3/2008 |
| WO | WO 2008/113364 A2 | 9/2008 |
| WO | WO 2008/124660 A2 | 10/2008 |
| WO | WO 2009/025854 A1 | 2/2009 |
| WO | WO 2009/045443 A2 | 4/2009 |
| WO | WO 2009/148623 A2 | 12/2009 |
| WO | WO 2010/088633 A2 | 8/2010 |
| WO | WO 2010/101648 A1 | 9/2010 |
| WO | WO 2011/017809 A1 | 2/2011 |
| WO | WO 2011/035321 A1 | 3/2011 |
| WO | WO 2011/079279 A2 | 6/2011 |
| WO | WO 2012/058378 A1 | 5/2012 |
| WO | WO 2012/068274 A1 | 5/2012 |
| WO | WO 2012/079232 A1 | 6/2012 |
| WO | WO 2012/100248 A1 | 7/2012 |
| WO | WO 2012/143377 A1 | 10/2012 |
| WO | WO 2012/154944 A1 | 11/2012 |
| WO | WO 2012/172069 A1 | 12/2012 |
| WO | WO 2013/175474 A2 | 11/2013 |
| WO | WO 2014/023329 A1 | 2/2014 |
| WO | WO 2014/023732 A1 | 2/2014 |
| WO | WO 2014/062621 A1 | 4/2014 |
| WO | WO 2014/108571 A2 | 7/2014 |
| WO | WO 2014/113467 A1 | 7/2014 |
| WO | WO 2014/128245 A1 | 8/2014 |

OTHER PUBLICATIONS

European Patent Office Partial Search Report for Application No. 16815395.5 dated Jan. 10, 2019 (16 pages).
European Patent Office Extended Search Report for Application No. 16815395.5 dated Apr. 15, 2019 (12 pages).
Anastas et al., "WNT signalling pathways as therapeutic targets in cancer," Nature Reviews Cancer, 2013, 13(1):11-26.
Andrews et al., "The biology and toxicology of molluscicides, Bayluscide," Pharmac. Ther., 1983, 19, 245-95.
Arend et al., "Inhibition of Wnt/β-catenin pathway by niclosamide: A therapeutic target for ovarian cancer," Gynecologic Oncology, 2014, 134, 112-120.
Barker et al., "Mining the Wnt pathway for cancer therapeutics," Nature Reviews Drug Discovery, 2006, 5, 997-1014.
Besancon et al.,"Cancer Stem Cells: The Emerging Challenge of Drug Targeting," Current Medicinal Chemistry, 2009, 16, 394-416.
Bhushan et al., "Bionanotherapeutics: niclosamide encapsulated albumin nanoparticles as a novel drug delivery system for cancer therapy ," RSC Advances, 2015, 5, 12078-12086.
C.T.F.A. Cosmetic Ingredient Handbook, 1992, 587-592.
CAS Registry No. 446874-81-3.
Chang et al., "Pharmacokinetics of Anti-SARS-CoV Agent Niclosamide and Its Analogs in Rats," Journal of Food and Drug Analysis, 2006, 14(4):329-333.
Chen et al., "Application of Lipid-Based Formulations in Drug Discovery," Journal of Medicinal Chemistry, 2012, 55, 7945-7956.
Chen et al., "Discovery of O-Alkylamino-Tethered Niclosamide Derivatives as Potent and Orally Bioavailable Anticancer Agents," ACS Medicinal Chemistry Letters, 2013, 4, 180-185.
Chen et al., "Dishevelled 2 Recruits β-Arrestin 2 to Mediate Wnt5A-Stimulated Endocytosis of Frizzled 4," Science, 2003, 301, 1391-1394.
Chen et al., "Small molecule—mediated disruption of Wnt-dependent signaling in tissue regeneration and cancer," Nature Chemical Biology, 2009, 5, 100-107.

Chen et al., "The Anti-Helminthic Niclosamide Inhibits Wnt/Frizzled1 Signaling," Biochemistry, 2009, 48, 10267-10274.
Coombs et al., "Wnt Signaling in Development, Disease and Translational Medicine," Current Drug Targets, 2008, 9, 513-531.
DiMeo et al., "A novel lung metastasis signature links Wnt signaling with cancer cell self-renewal and epithelial-mesenchymal transition in basal-like breast cancer," Cancer Research, 2009, 69(13):5364-5373.
Fonseca et al., "Structure-Activity Analysis of Niclosamide Reveals Potential Role for Cytoplasmic pH in Control of Mammalian Target of Rapamycin Complex 1 (mTORC1) Signaling," J. Biol. Chem. 2012, 287, 17530-17545.
Frayha et al., "The mechanisms of action of antiprotozoal and anthelmintic drugs in man," General Pharmacology, 1997, 28, 273-299.
Grifasi et al., "Using Salt Cocrystals to Improve the Solubility of Niclosamide," Crystal Growth & Design, 2015, 15, 1939-1948.
Guo et al., "Enantioselective addition of diethylzinc to benzaldehyde catalyzed by chiral titanate complexes with helical ligands," Tetrahedron, 1997, 53(12): 4145-4158.
Haq et al., "Oncogenic BRAF Regulates Oxidative Metabolism via PGC1α and MITF," Cancer Cell, 2013, 23, 302-315.
Howe et al., "Wnt Signaling and Breast Cancer," Cancer Biology and Therapy, 2004, 3(1):36-41.
Huang et al., "Tankyrase inhibition stabilizes axin and antagonizes Wnt signalling," Nature, 2009, 461, 614-620.
Imperi et al., "New Life for an Old Drug: the Anthelmintic Drug Niclosamide Inhibits Pseudomonas aeruginosa Quorum Sensing," Antimicrob Agents Chemother, 2013, 57, 996-1005.
IUPAC, "Rules for the Nomeclature of Organic Chemistry, Section E: Stereochemistry, Recommendations 1974," Pure Appl. Chem., 1976, 45:13-30.
Jin et al., "Antineoplastic Mechanisms of Niclosamide in Acute Myelogenous Leukemia Stem Cells: Inactivation of the NF-κb Pathway and Generation of Reactive Oxygen Species," Cancer Res, 2010, 70, 2516-2527.
Jin, "The WNT signalling pathway and diabetes mellitus," Diabetologia, 2008, 51, 1771-1780.
Jurgeit et al., "Niclosamide Is a Proton Carrier and Targets Acidic Endosomes with Broad Antiviral Effects," PLoS Pathogens, 2012, 8, e1002976, 14 pages.
Kasim et al., "Molecular Properties of WHO Essential Drugs and Provisional Biopharmaceutical Classification," Molecular Pharmaceutics, 2004, 1, 85-96.
Khanim et al., "Redeployment-based drug screening identifies the anti-helminthic niclosamide as anti-myeloma therapy that also reduces free light chain production," Blood Cancer Journal, 2011, 1, e39, 12 pages.
Lee et al., "Structure—activity relationships of antitubercular salicylanilides consistent with disruption of the proton gradient via proton shuttling," Bioorganic & Medicinal Chemistry, 2013, 21(1):114-126.
Li et al., "Multi-targeted therapy of cancer by niclosamide: A new application for an old drug," Cancer Lett, 2014, 349, 8-14.
Li et al., "Niclosamide Overcomes Acquired Resistance to Erlotinib through Suppression of STAT3 in Non—Small Cell Lung Cancer," Mol Cancer Ther, 2013, 12, 2200-2212.
Liu et al., "Niclosamide Inhibits Androgen Receptor Variants Expression and Overcomes Enzalutamide Resistance in Castration-Resistant Prostate Cancer," Clinical Cancer Research, 2014, 20, 3198-3210.
Londono-Joshi et al., "Effect of Niclosamide on Basal-like Breast Cancers," Mol Cancer Ther, 2014, 13, 800-811.
Lu et al., "Niclosamide Suppresses Cancer Cell Growth by Inducing Wnt Co-Receptor LRP6 Degradation and Inhibiting the Wnt/β-Catenin Pathway," PLoS One, 2011, 6, e29290, 8 pages.
MacDonald et al., "Wnt/β-Catenin Signaling: Components, Mechanisms, and Diseases," Developmental Cell, 2009, 17, 9-26.
Mallinger et al., "Discovery of Potent, Orally Bioavailable, Small-Molecule Inhibitors of WNT Signaling from a Cell-Based Pathway Screen," Journal of Medicinal Chemistry 2015, 58, 1717-1735.
McCutcheon's vol. 1, Emulsifiers & Detergents, North American Edition, 1994, pp. 236-239.

(56) References Cited

OTHER PUBLICATIONS

Meireles et al., "Discovery of modulators of protein-protein interactions: current approaches and limitations," Curr. Top. Med. Chem., 2011, 11, 248-257.
Merschjohann et al., "In vitro trypanocidal activity of the antihelminthic drug niclosamide," Experimental Parasitology, 2008, 118, 637-40.
Michelotti et al., "NAFLD, NASH and liver cancer," Nat Rev Gastroenterol Hepatol, 2013, 10, 656-665.
Minde et al., "Large Extent of Disorder in Adenomatous Polyposis Coli Offers a Strategy to Guard Wnt Signalling against Point Mutations," PLoS One, 2013, 8(10):e77257, 9 pages.
Modern Pharmaceutics, "Disperse Systems: Solubilized Products, Suspensions, and Emulsions," Chapters 9, Banker & Rhodes, eds. (1979) pp. 329-357.
Modern Pharmaceutics, "Solid Oral Dosage Forms," Chapters 10, Banker & Rhodes, eds. (1979) pp. 359-427.
Mook et al., "Small molecule modulators of Wnt/β-catenin signaling," Bioorg Med Chem Lett 2013, 23, 2187-2191.
Osada et al., "Antihelminth Compound Niclosamide Downregulates Wnt Signaling and Elicits Antitumor Responses in Tumors with Activating APC Mutations," Cancer Research, 2011, 71, 4172-4182.
Pearson et al., "Niclosamide Therapy for Tapeworm Infections," Annals of Internal Medicine, 1985, 102, 550-551.
Perry et al., "Controlled-release mitochondrial protonophore reverses diabetes and steatohepatitis in rats," Science, 2015, 347, 1253-1256.
Piccaro et al., "Activities of Drug Combinations against Mycobacterium tuberculosis Grown in Aerobic and Hypoxic Acidic Conditions," Antimicrob Agents Chemother, 2013, 57, 1428-1433.
Pubchem, Substance Record for SID 136335407, 2012.
Pubchem, Substance Record for SID 198943659, 2014.
Pubchem, Substance Record for SID 60958405, 2009.
Rajamuthiah et al., "Repurposing Salicylanilide Anthelmintic Drugs to Combat Drug Resistant *Staphylococcus aureus*," PLoS One, 2015, 10, e0124595, 19 pages.
Remington's Pharmaceutical Sciences, 15th Ed, 1975, pp. 335-337.
Ren et al., "Identification of Niclosamide as a New Small-Molecule Inhibitor of the STAT3 Signaling Pathway," ACS Medicinal Chemistry Letters, 2010, 1, 454-459.
Roesch et al., "Overcoming Intrinsic Multidrug Resistance in Melanoma by Blocking the Mitochondrial Respiratory Chain of Slow-Cycling JARID1B$^{high}$ Cells," Cancer Cell, 2013, 23, 811-825.
Sack et al., "Novel Effect of Antihelminthic Niclosamide on S100A4-Mediated Metastatic Progression in Colon Cancer," Journal of the National Cancer Institute, 2011, 103, 1018-1036.
Sebio et al., "The potential of targeting Wnt/β-catenin in colon cancer," Expert Opinion on Therapeutic Targets, 2014, 18, 611-615.
Strickley, "Solubilizing Excipients in Oral and Injectable Formulations," Pharmaceutical Research, 2004, 21, 201-230.
Strohecker et al., "Targeting Mitochondrial Metabolism by Inhibiting Autophagy in BRAF-Driven Cancers," Cancer Discovery, 2014, 4, 766-772.
Swan, "The pharmacology of halogenated salicylanilides and their anthelmintic use in animals," J. S. Afr. Vet. Assoc. 1999, 70, 61-70.
Taketo, "Shutting down Wnt signal-activated cancer," Nature Genetics, 2004, 36, 320-322.
Tao et al., "Niclosamide ethanolamine-induced mild mitochondrial uncoupling improves diabetic symptoms in mice," Nature Medicine, 2014, 20, 1263-1269.
Terada, "Uncouplers of oxidative phosphorylation," Environmental Health Perspectives, 1990, 87, 213-218.
Wang et al., "The autonomous notch signal pathway is activated by baicalin and baicalein but is suppressed by niclosamide in K562 cells," Journal of Cellular Biochemistry, 2009, 106, 682-692.
Weinbach et al., "Mechanism of Action of Reagents that uncouple Oxidative Phosphorylation," Nature, 1969, 221, 1016-1018.
WHO, "Specifications and Evaluations for Public Health Pesticides," World Health Organization, http://www.who.int/whopes/quality/en/Niclosamide.pdf.: Geneva, 2002, 24 pages.
WHO, "The Selection and Use of Essential Medicines," World Health Organization, Geneva, 2007, 172 pages.
Wieland et al., "Anticancer Effects of Niclosamide in Human Glioblastoma," Clinical Cancer Research, 2013, 19, 4124-4136.
Ye et al., "Design and evaluation of injectable niclosamide nanocrystals prepared by wet media milling technique," Drug Development and Industrial Pharmacy, 2015, 41(9):1416-1424.
Yin et al., "Normalization of CD4$^+$ T cell metabolism reverses lupus," Science Translational Medicine, 2015, 7, 274, 274ra18, 12 pages.
Yo et al., "Growth inhibition of ovarian tumor-initiating cells by niclosamide," Molecular Cancer Therapeutics, 2012, 11(8):1703-12.
Yuan et al., "Design, synthesis and antitumor activity of valproic acid salicylanilide esters," Yaoxue Xuebao, 2013, 48(6): 874-880.
International Search Report and Written Opinion for Application No. PCT/US2016/039295 dated Sep. 8, 2016 (19 pages).
European Patent Office Action for Application No. 16815395.5 dated Jul. 27, 2020 (4 pages).

CHEMICAL MODULATORS OF SIGNALING PATHWAYS AND THERAPEUTIC USE

CROSS-REFERENCE TO RELATED APPLICATIONS

This application is a national phase application under 35 U.S.C. § 371 of International Patent Application No. PCT/US2016/039295, filed on Jun. 24, 2016, which claims priority to U.S. Provisional Patent Application No. 62/184,133, filed on Jun. 24, 2015, and to U.S. Provisional Patent Application No. 62/188,131, filed on Jul. 2, 2015, and to U.S. Provisional Patent Application No. 62/193,935, filed on Jul. 17, 2015, the contents of each of which are hereby incorporated by reference in their entireties.

STATEMENT OF GOVERNMENT INTEREST

This invention was made with government support under Grant numbers R01-CA172570 awarded by the National Cancer Institute (NCI); 5K12-CA100639 awarded by the National Cancer Institute (NCI); and BC123289 awarded by the Department of Defense (DOD). The government has certain rights in the invention.

TECHNICAL FIELD

The present disclosure relates to compounds, compositions, and methods for treating Wnt/Frizzled related diseases and/or disorders, such as cancer.

BACKGROUND

Wnt proteins are secreted glycoproteins that bind and activate the seven transmembrane receptor Frizzled and single transmembrane receptors LRP5/6. Wnt binding to Frizzled and LRP5/6 results in activation of cytosolic proteins Disheveled (Dvl), leading to internalization of the Frizzled receptor. Downstream signaling events resulting from Wnt binding include the stabilization and translocation of cytosolic β-catenin proteins into the nucleus, activation of the transcription factor LEF/TCF and transcription of Wnt/β-catenin target genes.

The Wnt signaling pathway plays a key role in tissue development and homeostasis and is dysregulated in many diseases including cancer. For example, in colorectal cancer (CRC) more than 80% of all sporadic and hereditary cancers show hyperactivation of the pathway due to mutations in the adenomatous polyposis coli (APC) or the β-catenin gene. Given the importance of the Wnt signaling activity underlying tumor formation and metastasis, therapies against the Wnt signaling pathway are highly sought after.

Niclosamide, a drug approved by the FDA for use as an anthelminthic therapy, promotes Frizzled internalization. Studies have found that niclosamide downregulates Disheveled and β-catenin and inhibits colon cancer cell growth in vitro and in vivo. Whereas the pharmacokinetic properties of niclosamide are appropriate for use in the gut as an anthelmintic agent, its low solubility, low bioavailability and poor pharmacokinetic profile results in low plasma exposure when dosed orally.

Accordingly, there exists a need for modification of, or a synthetic analogue of, niclosamide that is well tolerated in vivo, and possesses drug-like properties that are appropriate for oral dosing to subjects in need of anticancer therapy.

SUMMARY OF THE INVENTION

In one aspect, disclosed is a method of treating a disease associated with dysregulation of the Wnt/Frizzled signaling pathway in a subject in need thereof, the method comprising administering to the subject an effective amount of a compound of formula (I), or a pharmaceutically acceptable salt thereof,

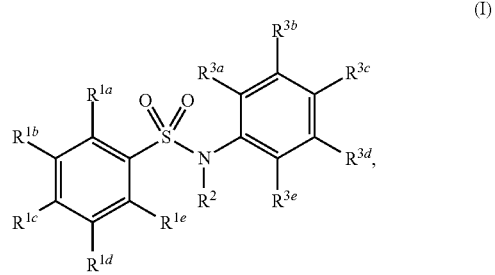

(I)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$. $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together form a six-membered aromatic ring; $R^2$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O—alkyl, —C(O)—O-alkenyl, and —C(O)—O-alkoxyalkyl, or $R^2$ and $R^{1e}$ together form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, $SO_2$—$R^9$ and $NR^8$—$SO_2$—$R^9$; $R^4$ is selected from hydrogen, —C(O)-alkyl, —C(O)-alkenyl, C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, —C(O)—O-alkoxyalkyl, —C(O)—NH-alkyl, and —C(O)-heterocycle; $R^5$, $R^6$ and $R^7$ are each independently selected from hydrogen, alkyl, —C(O)-alkyl, —C(O)-alkenyl, —C(O)—O-alkyl, —C(O)—O-alkenyl, —C(O)-alkoxyalkyl, —C(O)—NH—alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl.

In another aspect, disclosed is a method of treating a disease associated with dysregulation of the Wnt/Frizzled signaling pathway in a subject in need thereof, the method comprising administering to the subject an effective amount of a compound of formula (II), or a pharmaceutically acceptable salt thereof,

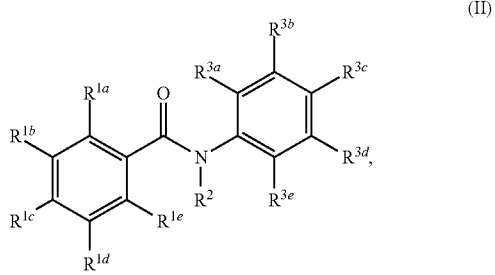

(II)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, OH, alkoxy, $OR^4$, $SR^5$, $NR^6R^7$, and $NR^8$—$SO_2$—$R^9$; or $R^{1b}$ and $R^{1c}$, $R^{1c}$ and $R^{1d}$, or $R^{1d}$ and $R^{1e}$ together form a six-membered aromatic ring; $R^2$ is selected from hydrogen, —C(O)-alkyl, —C(O)—O-alkyl, —C(O)— alkenyl, —C(O)—O-alkenyl, —C(O)-alkoxyalkyl, —C(O)—O-alkoxyalkyl, —C(O)-heteroalkyl, —C(O)-heteroaryl, —C(O)—O-heteroalkyl, and —C(O)—O-heteroaryl, or $R^2$ and $R^{1e}$ together form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, alkoxy, OH, $OR^4$, $SR^5$, $NR^6R^7$, $SO_2$—$R^9$, and $NR^8$—$SO_2$—$R^9$; $R^4$ is selected from —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O-alkyl, —C(O)—O-alkenyl, and —C(O)—O— alkoxyalkyl; $R^5$, $R^6$ and R are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl; provided that when $R^4$ is —C(O)-alkyl, —C(O)-alkenyl, —C(O)-heteroalkyl, —C(O)-heteroaryl, or —C(O)— alkoxyalkyl, $R^2$ is —C(O)-alkyl, —C(O)—O-alkyl, —C(O)-alkenyl, —C(O)—O-alkenyl, —C(O)— alkoxyalkyl, —C(O)—O-alkoxyalkyl, —C(O)-heteroalkyl, —C(O)-heteroaryl, —C(O)—O— heteroalkyl, and —C(O)—O-heteroaryl.

In another aspect, disclosed is a method of treating a disease associated with dysregulation of the Wnt/Frizzled signaling pathway in a subject in need thereof, the method comprising administering to the subject an effective amount of a compound of formula (III), or a pharmaceutically acceptable salt thereof,

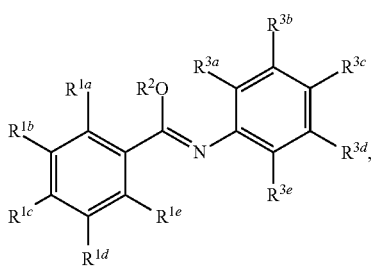

(III)

wherein, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, OH, alkoxy, $OR^4$, $SR^5$, $NR^6R^7$, and $NR^8$—$SO_2$—$R^9$; or $R^{1b}$ and $R^{1c}$ together form a six-membered aromatic ring; $R^2$ is selected from —C(O)-alkyl, —C(O)—O-alkyl, —C(O)-alkenyl, —C(O)—O-alkenyl, —C(O)— alkoxyalkyl, —C(O)—O-alkoxyalkyl, —C(O)-heteroalkyl, —C(O)-heteroaryl, —C(O)—O— heteroalkyl, and —C(O)—O-heteroaryl; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, alkoxy, OH, $OR^4$, $SR^5$, $NR^6R^7$, $SO_2$—$R^9$, and $NR^8$—$SO_2$—$R^9$; $R^4$ is selected from —C(O)-alkyl, —C(O)-alkenyl, —C(O)-heteroalkyl, —C(O)— heteroaryl, —C(O)-alkoxyalkyl, —C(O)—O-heteroalkyl, —C(O)—O-heteroaryl, —C(O)—O-alkyl, —C(O)—O-alkenyl, and —C(O)—O-alkoxyalkyl; $R^5$, $R^6$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl.

In another aspect, disclosed is a method of treating a disease associated with dysregulation of the Wnt/Frizzled signaling pathway in a subject in need thereof, the method comprising administering to the subject an effective amount of a compound selected from the group consisting of: 4-chloro-2-((2-chloro-4-(trifluoromethyl)phenyl)carbamoyl)phenyl acetate; 4-chloro-2-((2-chloro-4-nitrophenyl)carbamoyl)phenyl octanoate; 4-chloro-2-((2-chloro-4-nitrophenyl)carbamoyl)phenyl heptanoate; 4-chloro-2-((2-chloro-4-nitrophenyl)carbamoyl)phenyl isobutyrate; tert-butyl (4-chloro-2-((2-chloro-4-nitrophenyl)carbamoyl)phenyl) succinate; 4-chloro-2-((2-chloro-4-nitrophenyl)carbamoyl)phenyl 2-propylpentanoate; 4-chloro-2-((2-chloro-4-nitrophenyl)carbamoyl)phenyl 6-(2,5-dioxo-2,5-dihydro-1H-pyrrol-1-yl)hexanoate; 4-chloro-2-((2-chloro-4-nitrophenyl)carbamoyl)phenyl oleate; 4-chloro-2-((2-chloro-4-nitrophenyl)carbamoyl)phenyl (9Z,12Z)-octadeca-9,12-dienoate; 4-chloro-2-((2-chloro-4-nitrophenyl)carbamoyl)phenyl morpholine-4-carboxylate; 5-chloro-2-hydroxy-N-phenylbenzamide; N-(4-acetylphenyl)-5-chloro-2-hydroxybenzamide; N-(4-carbamoylphenyl)-5-chloro-2-hydroxybenzamide; N-(4-benzoylphenyl)-5-chloro-2-hydroxybenzamide; 5-chloro-2-hydroxy-N-(4-(phenylcarbamoyl)phenyl)benzamide; 5-chloro-N-(2-chloro-4-(trifluoromethyl)phenyl)-2-hydroxybenzamide; 5-chloro-2-hydroxy-N-(4-(trifluoromethyl)phenyl)benzamide; 5-chloro-2-hydroxy-N-(3-(trifluoromethyl)phenyl)benzamide; 5-chloro-N-(2-fluoro-4-(trifluoromethyl)phenyl)-2-hydroxybenzamide; 5-chloro-N-(4-chlorophenyl)-2-hydroxybenzamide; 5-chloro-N-(3-chlorophenyl)-2-hydroxybenzamide; 5-chloro-N-(2-chlorophenyl)-2-hydroxybenzamide; 5-chloro-N-(2,4-dichlorophenyl)-2-hydroxybenzamide; 5-chloro-N-(2,5-dichlorophenyl)-2-hydroxybenzamide; 5-chloro-N-(3,5-dichlorophenyl)-2-hydroxybenzamide; 5-chloro-N-(3,4-dichlorophenyl)-2-hydroxybenzamide; 5-chloro-N-(2,6-dichlorophenyl)-2-hydroxybenzamide; 5-chloro-N-(4-fluorophenyl)-2-hydroxybenzamide; 5-chloro-N-(2,4-difluorophenyl)-2-hydroxybenzamide; 5-chloro-N-(2,6-difluorophenyl)-2-hydroxybenzamide; 5-chloro-N-(2-chloro-4-fluorophenyl)-2-hydroxybenzamide; 5-chloro-N-(3-chloro-4-fluorophenyl)-2-hydroxybenzamide; 5-chloro-2-hydroxy-N-methyl-N-(4-(trifluoromethyl)phenyl)benzamide; 5-chloro-2-hydroxy-N-(4-(trifluoromethyl)benzyl)benzamide; 5-chloro-2-hydroxy-N-(4-(trifluoromethyl)benzoyl)benzamide; 6-chloro-3-(2-chloro-4-(trifluoromethyl)phenyl)-2H-benzo[e][1,3]oxazine-2,4(3H)-dione; 6-chloro-3-(4-(trifluoromethyl)phenyl)-2H-benzo[e][1,3]oxazine-2,4(3H)-dione; 6-chloro-3-(2-chloro-4-nitrophenyl)-2H-benzo[e][1,3]oxazine-2,4(3H)-dione; 2-((4-methylphenyl)sulfonamido)-N-(4-nitrophenyl)benzamide; 5-bromo-N-(4-bromophenyl)-2-hydroxybenzamide; N-(2-chloro-4-nitrophenyl)-4-hydroxy-[1,1'-biphenyl]-3-carboxamide; 5-chloro-2-hydroxy-N-(2-methyl-4-nitrophenyl)benzamide; N-(2-chloro-4-nitrophenyl)-2',4'-difluoro-4-hydroxy-[1,1'-biphenyl]-3- carboxamide; N-(2-chloro-4-(trifluoromethyl)phenyl)-2-hydroxy-1-naphthamide; N-(2-chloro-4-(trifluoromethyl)phenyl)-3-hydroxy-2-naphthamide; N-(2-chloro-4-(trifluoromethyl)phenyl)-1-hydroxy-2-naphthamide; N-(4-(benzyloxy)-3-chlorophenyl)-5-chloro-2-hydroxybenzamide; N-(2-chloro-4-nitrophenyl)-2-hydroxy-4,5-dimethoxybenzamide; N-(4-(benzyloxy)-3-chlorophenyl)-2-hydroxy-4,5-dimethoxybenzamide; N-(2-bromo-4-(trifluoromethyl)phenyl)-5-chloro-2-hydroxybenzamide; 5-bromo-2-((4-methylphenyl)sulfonamido)-N-(4-(trifluoromethyl)phenyl)benzamide; 5-chloro-2-hydroxy-N-(4-nitro-2-((10,17,24-trioxo-28-(2-oxohexahydro-1H-thieno[3,4-d]imidazol-4-yl)-3,6-dioxa-9,16,23-triazaoctacosyl)oxy)phenyl)benzamide; 4-hydroxy-N-(4-(trifluoromethyl)phenyl)quinoline-3-carboxamide; N-(2-(allyloxy)-4-nitrophenyl)-5-chloro-2-hydroxybenzamide; 5-chloro-N-(2-chloro-4-nitrophenyl)-2-((4-methylphenyl)sulfonamido)benzamide; 5-chloro-2-hydroxy-N-(4-nitro-2-(2-oxoethoxy)phenyl)benzamide; 5-chloro-N-(3-fluoro-4-nitrophenyl)-2-hydroxybenzamide; 5-chloro-2-hydroxy-N-(4-nitro-2-(prop-2-yn-1-yloxy)phenyl)benzamide; 5-chloro-2-hydroxy-N-(3-morpholino-4-nitrophenyl)benzamide; 5-chloro-2-hydroxy-N-(3-methoxy-4-nitrophenyl)benzamide; 2-((2-(allyloxy)-4-nitrophenyl)carbamoyl)-4-chlorophenyl acetate; 4-chloro-2-((2-chloro-4-nitrophenyl)carbamoyl)phenyl stearate; 5-chloro-N-(3-chloro-4-nitrophenyl)-2-hydroxybenzamide; N-(4-azido-2-(prop-2-yn-1-yloxy)phenyl)-5-chloro-2-hydroxybenzamide; 5-chloro-N-(3-chloro-4-(trifluoromethyl)phenyl)-2-hydroxybenzamide; 5-chloro-N-(2-(hex-5-yn-1-yloxy)-4-nitrophenyl)-2-hydroxybenzamide; 5-chloro-N-(2-chloro-4-nitrophenyl)-2-(methylsulfonamido)benzamide; 5-chloro-N-(2-chloro-4-(trifluoromethyl)phenyl)-2-(methylsulfonamido)benzamide; N-(2-chloro-4-nitrophenyl)-2-hydroxy-4-methoxybenzamide; 5-chloro-N-(2-chloro-4-nitrophenyl)-2-hydroxy-4-methoxybenzamide; 5-chloro-N-(2-chloro-4-fluorophenyl)-2-hydroxy-4-methoxybenzamide; 5-chloro-N-(3-chlorophenyl)-2-hydroxy-4-methoxybenzamide; 6-chloro-3-(2-fluoro-4-(trifluoromethyl)phenyl)-2H-benzo[e][1,3]oxazine-2,4(3H)-dione; 5-chloro-2-hydroxy-N-(3-nitrophenyl)benzamide; 5-chloro-2-hydroxy-N-(2-nitrophenyl)benzamide; 2-(2-aminoethoxy)-5-chloro-N-(2-chloro-4-nitrophenyl)benzamide; 5-chloro-N-(2-chloro-4-(phenylsulfonyl)phenyl)-2-hydroxybenzamide; 5-chloro-N-(2-chloro-4-((4-chlorophenyl)sulfonyl)phenyl)-2-hydroxybenzamide; 5-chloro-N-(2-chloro-4-tosylphenyl)-2-hydroxybenzamide; 5-chloro-N-(2-chloro-4-(4-methylbenzoyl)phenyl)-2-hydroxybenzamide; and 6-chloro-3-(2-fluoro-4-(trifluoromethyl)phenyl)-2H-benzo[e][1,3]oxazine-2,4(3H)-dione, or a pharmaceutically acceptable salt thereof.

In another aspect, disclosed are methods for treating cancer in a subject in need thereof, the method comprising identifying a subject with dysregulated Wnt/Frizzled signaling pathway; and administering to the subject with dysregulated Wnt/Frizzled signaling pathway effective amount of a compound disclosed herein or a pharmaceutically acceptable salt thereof to a subject in need thereof.

In another aspect, disclosed are methods of modulating the Wnt/Frizzled signaling pathway in a subject, the method comprising administering to the subject an effective amount of a compound.

In another aspect, disclosed are pharmaceutical compositions comprising at least one pharmaceutically acceptable carrier and an effective amount of a compound disclosed herein.

DETAILED DESCRIPTION

Figure 1:
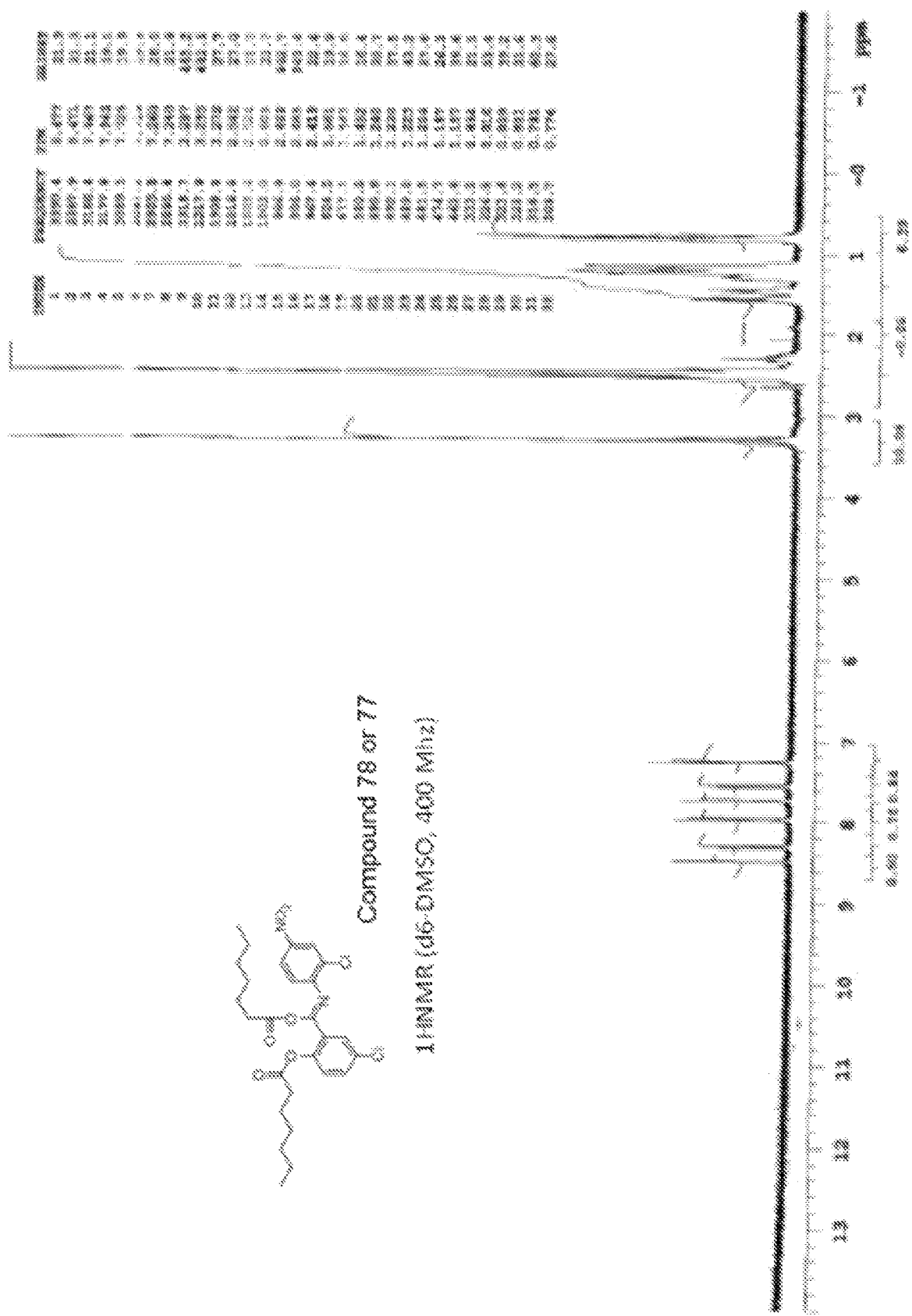
FIG. 1 is a $^1$H-NMR spectrum of an exemplary compound.

Disclosed herein are methods of treating a disease associated with dysregulation of the Wnt/Frizzled signaling pathway. The Wnt/Frizzled signaling pathway has been implicated in a number of different diseases and/or disorders such as cancer and metabolic diseases such as type II diabetes. Based on the multifunctional bioactivity of the Wnt inhibitor niclosamide, this pathway may also be implicated in other diseases and/or disorders such as lupus, bacterial and viral infection, nonalcoholic steatohepatitis (NASH) and nonalcoholic fatty liver disease (NAFLD). Treatment of the disease associated with dysregulation of the Wnt/Frizzled signaling pathway may be accomplished by use of the compounds disclosed herein. Accordingly, the compounds disclosed herein are inhibitors of the Wnt/Frizzled signaling pathway.

As part of an effort to discover Wnt inhibitors with improved potency, selectivity and pharmacokinetic properties for clinical evaluation, compounds were synthesized and evaluated. Surprisingly, it was found that certain derivatives of niclosamide possess a greatly improved pharmacokinetic profile over niclosamide when dosed orally to mice.

In particular, it was surmised that modification of the salicylamide group of niclosamide would have an effect on its pharmacokinetic profile and possibly improve the exposure of the inhibitors. The phenolic OH group is a potential site of glucuronidation and clearance. Moreover, the calculated pKa of the OH group (pKa=6.8) indicated that the molecule would be substantially ionized at the pH of intestinal fluid (pH=4-8), and the pH of blood (pH=7.4). Ionization of the OH group would be expected to limit exposure by reducing the permeability of the molecule and limit the volume of distribution, both of which could be expected to reduce exposure. In addition, the salicylamide moiety possesses two hydrogen bond donors that could be expected to reduce permeability. In view of the foregoing, derivatives of niclosamide were synthesized that converted the phenolic hydroxyl to an ester. These derivatives demonstrated a surprising improvement increase in plasma exposure when dosed orally to mice. Furthermore, no observable adverse effects were observed over multiple weeks of oral dosing of the niclosamide derivatives. The ability of some of the disclosed compounds to metabolize to niclosamide in a manner that increases the exposure of niclosamide when dosed orally provides a valuable therapeutic agent.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

A "disease associated with dysregulation of the Wnt/Frizzled signaling pathway," as used herein, is a disease in which the Wnt/Frizzled signaling pathway is dysregulated. Certain exemplary Wnt/Frizzled-related diseases include, but are not limited to, cardiovascular disease, neoplasm, obesity, osteoporosis, neuron degeneration, cancer, diabetes, and disorders in wound healing and tissue repair. The Wnt/Frizzled signaling pathway may be considered dysregulated when, for example, diseased tissue and/or cells comprise at least one of: increased levels of β-catenin; increased LEF/TCF-mediated transcription; increased levels of one or more Wnt proteins, including, but not limited to, Wnt3A; increased levels of Frizzled; and/or increased levels of Disheveled; as compared to normal tissue and/or cells. As used herein, the term "tissue" includes all biological tissues, including, but not limited to, organ tissue, tumor tissue, skin, blood, etc.

The term "effective amount," as used herein, refers to a dosage of the compounds or compositions effective for eliciting a desired effect. This term as used herein may also refer to an amount effective at bringing about a desired in vivo effect in an animal, preferably, a human, such as treatment of a disease.

The term "treatment", as used herein in the context of treating a condition, pertains generally to treatment and therapy, whether of a human or an animal (e.g. in veterinary applications), in which a desired therapeutic effect is achieved. For example, treatment includes prophylaxis and can ameliorate or remedy the condition, disease, or symptom, or treatment can inhibit the progress of the condition or disease (e.g., reduce the rate of disease/symptom progression or halt the rate of disease/symptom progression).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "heteroarylalkyl" as used herein, refers to a heteroaryl group, as defined herein, appended to the parent molecular moiety through an alkylene group, as defined herein.

The term "heterocyclealkyl" as used herein, refers to a heterocycle group, as defined herein, appended to the parent molecular moiety through an alkylene group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkoxy" as used herein, means at least one alkyl group, as defined herein, is appended to the parent molecular moiety through an oxygen atom. Representative examples of alkoxy include, but are not limited to, methoxy, ethoxy, and isopropoxy.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "carboxyl" as used herein, means a carboxylic acid, or —COOH.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" as used herein, means Cl, Br, I, or F.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroalkyl," as used herein, means an alkyl group, as defined herein, in which at least one of the carbons of the alkyl group is replaced with a heteroatom, such as oxygen, nitrogen, and sulfur.

The term "hydroxyl" or "hydroxy" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated

2. METHODS OF TREATMENT

The disclosed compounds and compositions may be used in methods for treatment of Wnt/Frizzled related medical disorders and/or diseases. The methods of treatment may comprise administering to a subject in need of such treatment a composition comprising an effective amount of the compound of formula (I), the compound of formula (II), the compound of formula (III) or any compound disclosed herein.

The compositions can be administered to a subject in need thereof to modulate the Wnt/Frizzled signaling pathway for a variety of diverse biological processes. The present disclosure is directed to methods for administering the compositions to inhibit the Wnt/Frizzled signaling pathway, a pathway that plays a key role in tissue development and homeostasis and is dysregulated in many diseases including cancer and metabolic diseases such as type II diabetes. Based on the multifunctional bioactivity of the Wnt inhibitor niclosamide, this pathway may also be implicated in other diseases and/or disorders such as lupus, bacterial and viral infection, nonalcoholic steatohepatitis (NASH) and nonalcoholic fatty liver disease (NAFLD). Accordingly, the disclosed compounds and compositions may be administered to a subject for the treatment of cancer, type II diabetes, lupus, bacterial and viral infection, nonalcoholic steatohepatitis (NASH) and nonalcoholic fatty liver disease (NAFLD).

The compositions may be useful for treating and preventing certain diseases and disorders in humans and animals related to Wnt/Frizzled dysfunction. Treatment or prevention of such diseases and disorders can be effected by inhibiting the Wnt/Frizzled signaling pathway in a subject, by administering a compound or composition of the disclosure, either alone or in combination with another active agent as part of a therapeutic regimen to a subject in need thereof.

In certain embodiments, provided are methods of identifying a subject with a disease associated with dysregulation of the Wnt/Frizzled signaling pathway. The methods may comprise determining the level of at least one protein in a sample from a subject, wherein the protein is involved in the Wnt/Frizzled signaling pathway, and comparing the level of the protein to a standard level. An increased level of the protein may be indicative of a subject having a Wnt/Frizzled-related disease.

The methods of treatment may comprise determining the level of at least one protein in a sample from a subject, wherein the protein is involved in the Wnt/Frizzled signaling pathway, and comparing the level of the protein to a standard level, wherein an increased level of the protein may be indicative of a subject having a disease associated with dysregulation of the Wnt/Frizzled signaling pathway, and further administering to the subject an inhibitor of the Wnt/Frizzled signaling pathway.

a. Cancer

Inhibition of the Wnt/Frizzled signaling pathway can lead to treatment and reduction of cancer or tumor growth, and/or reduce metastasis of cancerous or tumor cells. Accordingly, the disclosed compositions can be used in methods that treat and/or prevent cancer or tumors in a subject administered the compound. The method can treat cancer or tumor based growth and can be any type of cancer such as, but not limited to, breast cancer, melanoma, prostate cancer, lung cancer, ovarian cancer, esophageal cancer, glioblastoma, multiple myeloma, mantle cell lymphoma, liver cancer, leukemia, acute myelogenous leukemia, or a combination thereof.

In some embodiments, the administered composition to a subject in need thereof can mediate reduction, clearance or prevention of additional growth of tumor cells by inhibiting the Wnt/Frizzled signaling pathway, thereby reducing growth/proliferation or modifying differentiation of tumor cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

In certain embodiments, a subject in need of treatment for cancer may have at least one inactivating mutation of the Adenomatous Polyposis Coli (APC) gene, which is related to the Wnt/Frizzled signaling pathway. In certain embodiments, a subject in need of treatment for cancer may have at least one mutation of the β-catenin gene or overexpression of the β-catenin protein, or a combination thereof. In certain embodiments, a subject in need of treatment for cancer may have overexpression of Wnt ligands.

In certain embodiments, determining whether a cancer comprises a dysregulated Wnt/Frizzled signaling pathway may comprise detecting the level of one or more of Wnt, Frizzled, β-catenin, and/or Disheveled, and comparing the level to normal tissue and/or cells, In certain such embodiments, if the cancer comprises higher levels of Wnt, Frizzled, β-catenin and/or Disheveled as compared to normal tissue and/or cells, the cancer is predicted to respond to treatment with an inhibitor of the Wnt/Frizzled signaling pathway. In certain embodiments, determining whether a cancer comprises a dysregulated Wnt/Frizzled signaling pathway comprises detecting the level of LEF/TCF-mediated transcription as compared to LEF/TCF-mediated transcription in normal tissue and/or cells. In certain such embodiments, if the cancer comprises a higher level of LEF/TCF-mediated transcription as compared to normal tissue and/or cells, the cancer is predicted to respond to treatment with an inhibitor of the Wnt/Frizzled signaling pathway.

A variety of sources (Howe, et al. *Cancer Biology and Therapy* 2004, 3(1), 36-41; Taketo, M. Nature Genetics 2004, 36, 320-22; Minde et al. *PLOS ONE* 2013, 8(10), e77257) have reported that activity of the Wnt/Frizzled pathway is involved in the development of benign and malignant breast tumors. Furthermore, its presence is indicated with elevated levels of β-catenin in the nucleus and/or cytoplasm, and increased β-catenin expression is strongly correlated with poor prognosis in breast cancer patients. This accumulation may be due to several factors such as mutations in β-catenin, deficiencies in the β-catenin destruction complex, most frequently by mutations in structurally disordered regions of APC, overexpression of Wnt ligands, loss of inhibitors, and/or decreased activity of regulatory pathways. Breast tumors have also been seen to metastasize due to Wnt involvement in the epithelial-mesenchymal transition (EMT). Investigation of the metastasis of basal-like breast cancer to the lungs has shown that repression of Wnt/β-catenin signaling can prevent EMT, which can inhibit metastasis (DiMeo, et al. *Cancer Research* 2009, 69(13), 5364-5373).

Wnt signaling has also been implicated in the development of other cancers. Changes in CTNNB1 expression, which is the gene that encodes β-catenin, can be measured in not just breast cancer, but also colorectal cancer, melanoma, prostate cancer, lung cancer, and several other cancer types. Increased expression of Wnt ligand-proteins such as Wnt 1, Wnt2, and Wnt7A have been observed in the development of glioblastoma, esophageal cancer, and ovarian cancer respectively. Other proteins known to cause multiple types of cancer in the absence of proper functioning include ROR1, ROR2, SFRP4, Wnt5A, WIF1, and those of the TCF/LEF family (Anastas, et al. *Nature Reviews Cancer* 2012, 13 (1), 11-26).

Accordingly, the foregoing firmly implicate the Wnt/Frizzled signaling pathway in the biology of a variety of cancer types and distinguish it as a cancer target.

b. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

c. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present disclosure. The above combinations include combinations of a compound of the present disclosure not only with one other active compound, but also with two or more active compounds. For example, the compound of the disclosure can be combined with a variety of anti-cancer drugs and chemotherapeutics.

The disclosed compounds can be combined with the following, but not limited to, actinomycins, alkylating agents, anthracyclines, antifolates, antiestrogen agents, antimetabolites, anti-androgens, antimicrotubule agents, aromatase inhibitors, bleomycins, $Ca^{2+}$ adenosine triphosphate (ATP) ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs. Specific anti-cancer or chemotherapeutic agents that may be combined with a disclosed compound include actinomycin D, AG13736, alisertib, 17-allylamino-17-demethoxygeldanamycin, altretamine, 9-aminocamptothecin, N-(4-(3-amino-1H-indazol-4-yl)phenyl}-N'-(2-fluoro-5-methylphenyl) urea, N-(4-(4-aminothieno[2,3-d]pyrimidin-5-yl)phenyl)}-N'-(2-fluoro-5-(trifluoromethyl)phenyl)urea, anastozole, AP-23573, asparaginase, axitinib, azacitidine, bevacizumab, bicalutamide, bevacizumab, bleomycin a2, bleomycin b2, bortezemib, busulfan, campathecins, carboplatin, carmustine (BCNU), CB1093, CHOP (C: Cytoxan® (cyclophosphamide); H: Adriamycin® (hydroxydoxorubicin); O: Vincristine (Oncovin®); P: prednisone), chlorambucil, CHIR258, cilengitide, cisplatin, CNF-101, CNF-1001, CNF-2024, CP547632, crisnatol, cytarabine, cyclophosphamide, cytosine arabinoside, daunorubicin, dabrafenib, dacarbazine, dactinomycin, dasatinib, daunorubicin, deferoxamine, demethoxyhypocrellin A, depsipeptide, 17-dimethylaminoethylamino-17-demethoxygeldanamycin, docetaxel, doxifluridine, doxorubicin, EB 1089, enzastaurin, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzene-sulfonamide, hydroxyurea, idarubicin, ifosfamide, imatinab, interferon-a, interferon-y, IPI-504, irinotecan, KH 1060, lapatinib, leucovorin calcium, LAQ824, leuprolide acetate, letrozole, lomustine (CCNU), melphalan, mercaptopurine, methotrexate, 1-methyl-4-phyenylpyridinium, MG132, mitoxantrone, mitozolomide, MLN4924, MLN518, MS-275, mycophenolic acid, nedaplatin, oprelvekin, oxaliplatin, paclitaxel, PD98059, pazopanib, peplomycin, phtalocyanine, pirarubicin, plicamycin, procarbazine, PTK787, PU24FC1, PU3, radicicol, raloxifene, rapamycin, ratitrexed, pheuretinide, ribavirin, rituximab (Rituxin®), satraplatin, sorafenib, staurosporine, suberoylanilide hydroxamic acid, sunitinib, tamoxifen, taxol, temozolomide, temsirolimus, teniposide, thapsigargin, thioguanine, thrombospondin-1, tiazofurin, topotecan, trapoxin, treosulfan, trichostatin A, trimetrexate, triplatin tetranitrate, trofosfamide, tumor necrosis factor, valproic acid, vemurafenib, VER49009, verapamil, vertoporfin, vinblastine, vincristine, vindesine, vinorelbine vitamin D3, VX-680, zactima, ZK-EPO, zorubicin, trastuzumab, cetuximab, lambrolizumab, nivolumab or any combination thereof.

The disclosed compounds may be included in kits comprising the compound [e.g., one or more disclosed compound], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

3. COMPOUNDS

In one aspect, disclosed is a compound of formula (I):

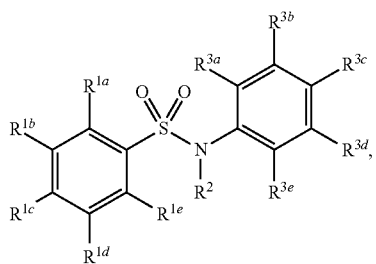

(I)

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$ and $NR^8$—$SO_2$—$R^9$; or $R^{1b}$ and $R^{1c}$, $R^{1c}$ and $R^{1d}$, or $R^{1d}$ and $R^{1e}$ together form a six-membered aromatic ring; $R^2$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, and —C(O)—O-alkoxyalkyl, or $R^2$ and $R^{1e}$ together form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, $OR^4$, $SR^5$, $NR^6R^7$, $SO_2$—$R^9$ and $NR^8$—$SO_2$—$R^9$; $R^4$ is selected from hydrogen, —C(O)-alkyl, —C(O)-alkenyl, —C(O)-alkoxyalkyl, —C(O)-heteroalkyl, —C(O)-heteroaryl, —C(O)—O-heteroalkyl, —C(O)—O-heteroaryl, —C(O)—O-alkyl, —C(O)—O-alkenyl, —C(O)—O-alkoxyalkyl, —C(O)—NH-alkyl, and —C(O)-heterocycle; $R^5$, $R^6$ and $R^7$ are each independently selected from hydrogen, alkyl, —C(O)-alkyl, —C(O)-alkenyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen and halogen; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^4$ is selected from hydrogen, —C(O)-alkyl, —C(O)-alkenyl, —C(O)-alkoxyalkyl, —C(O)—O-alkyl, —C(O)—O-alkenyl, —C(O)—O— alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen and halogen; $R^4$ is selected from —C(O)-alkyl, —C(O)-alkenyl, —C(O)-alkoxyalkyl, —C(O)—O-alkyl, —C(O)—O-alkenyl, —C(O)—O— alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^4$ is selected from —C(O)— alkyl, —C(O)-alkenyl, —C(O)—O-alkyl, and —C(O)—O-alkenyl; $R^8$ is selected from hydrogen and alkyl; and $R^9$ is selected from alkyl, aryl, and heteroaryl.

In certain embodiments, $R^{1a}$ is $OR^4$; $R^{1d}$ is halogen; $R^{1b}$, $R^{1c}$ and $R^{1e}$ are hydrogen; and $R^4$ is selected from —C(O)-alkyl, —C(O)-alkenyl, —C(O)-alkoxyalkyl, —C(O)—O-alkyl, —C(O)—O-alkenyl, —C(O)—O-alkoxyalkyl, —C(O)—NH-alkyl, and —C(O)-heterocycle.

In certain embodiments, $R^{1a}$ is $OR^4$; $R^{1d}$ is halogen; $R^{1b}$, $R^{1c}$ and $R^{1e}$ are hydrogen; and $R^4$ is selected from —C(O)-alkyl, —C(O)-alkenyl, —C(O)—O-alkyl, and —C(O)—O-alkenyl.

In certain embodiments, $R^2$ is selected from hydrogen, —C(O)-alkyl, —C(O)-alkenyl, —C(O)—O-alkenyl and —C(O)—O-alkyl.

In certain embodiments, $R^2$ is selected from —C(O)-alkyl, —C(O)-alkenyl, —C(O)—O— alkenyl and —C(O)—O-alkyl.

In certain embodiments, $R^2$ and $R^{1e}$ together form a 5 to 8-membered ring. In certain embodiments, $R^2$ and $R^{1e}$ together form a 5-membered ring. In certain embodiments, $R^2$ and $R^{1e}$ together form a 6-membered ring. In certain embodiments, $R^2$ and $R^{1e}$ together form a 7-membered ring. In certain embodiments, $R^2$ and $R^{1e}$ together form an 8-membered ring.

In certain embodiments, $R^{1a}$, $R^{1c}$ and $R^{1d}$ are hydrogen; $R^{1b}$ is halogen; and $R^2$ and $R^{1e}$ together form a 5 to 8-membered ring. In certain embodiments, $R^2$ and $R^{1e}$ together form a 5-membered ring. In certain embodiments, $R^2$ and $R^{1e}$ together form a 6-membered ring. In certain embodiments, $R^2$ and $R^{1e}$ together form a 7-membered ring. In certain embodiments, $R^2$ and $R^{1e}$ together form an 8-membered ring.

In certain embodiments, $R^{3a}$, $R^{3b}$, $R^{3c}$, $R^{3d}$ and $R^{3e}$ are independently selected from hydrogen, halogen, nitro, $SO_2$—$R^9$ and haloalkyl; and $R^9$ is selected from alkyl, aryl, and heteroaryl.

In certain embodiments, one of $R^{1a}$, $R^{1b}$, $R^{1c}$, $R^{1d}$ and $R^{1e}$ is $OR^4$ or $NR^8$—$SO_2$—$R^9$, and; $R^2$ is selected from hydrogen, —C(O)-alkyl, —C(O)-alkenyl, —C(O)—O-alkenyl and —C(O)—O— alkyl; $R^{3a}$, $R^{3b}$, $R^{3c}$, $R^{3d}$ and $R^{3e}$ are independently selected from hydrogen, halogen, nitro, $SO_2$—$R^9$ and haloalkyl; $R^4$ is selected from hydrogen, —C(O)-alkyl, —C(O)-alkenyl, —C(O)— alkoxyalkyl, —C(O)—O-alkyl, —C(O)—O-alkenyl, —C(O)—O- alkoxyalkyl, —C(O)—NH-alkyl, and —C(O)-heterocycle; $R^8$ is selected from hydrogen and alkyl; and $R^9$ is selected from alkyl, aryl, and heteroaryl.

In certain embodiments, one of $R^{1a}$ and $R^{1e}$ is $OR^4$ or $NR^8$—$SO_2$—$R^9$; $R^{1b}$, $R^{1c}$, and $R^{1d}$ are independently selected from hydrogen, halogen, and $OR^4$; $R^2$ is selected from hydrogen, —C(O)-alkyl, —C(O)-alkenyl, —C(O)—O-alkenyl and —C(O)—O-alkyl; $R^{3a}$, $R^{3b}$, $R^{3c}$, $R^{3d}$ and $R^{3e}$ are independently selected from hydrogen, halogen, nitro, $SO_2$—$R^9$ and haloalkyl; $R^4$ is selected from hydrogen, —C(O)-alkyl, —C(O)-alkenyl, —C(O)-alkoxyalkyl, —C(O)—O-alkyl, —C(O)—O— alkenyl, —C(O)—O-alkoxyalkyl, —C(O)—NH-alkyl, and —C(O)-heterocycle; $R^8$ is selected from hydrogen and alkyl; and $R^9$ is selected from alkyl, aryl, and heteroaryl.

Representative compounds of formula (I) include, but are not limited to:

5-chloro-N-(2-chloro-4-(trifluoromethyl)phenyl)-2-hydroxybenzenesulfonamide;

or a pharmaceutically acceptable salt thereof.

In another aspect, disclosed is a compound of formula (II):

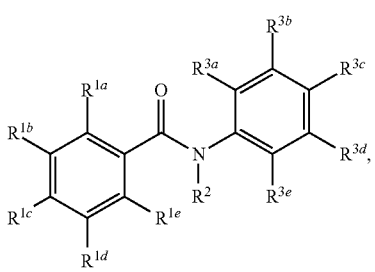

(II)

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, OH, alkoxy, $OR^4$, $SR^5$, $NR^6R^7$, and $NR^8$—$SO_2$—$R^9$; or $R^{1b}$ and $R^{1c}$, $R^{1c}$ and $R^{1d}$, or $R^{1d}$ and $R^{1e}$ together form a six-membered aromatic ring; $R^2$ is selected from hydrogen, —C(O)-alkyl, —C(O)—O-alkyl, —C(O)-alkenyl, —C(O)—O-alkenyl, —C(O)-alkoxyalkyl, —C(O)—O-alkoxyalkyl, —C(O)-heteroalkyl, —C(O)-heteroaryl, —C(O)—O-heteroalkyl, and —C(O)—O-heteroaryl, or $R^2$ and $R^{1e}$ together form a ring; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, alkoxy, OH, $OR^4$, $SR^5$, $NR^6R^7$, $SO_2$—$R^9$, and $NR^8$—$SO_2$—$R^9$; $R^4$ is selected from —C(O)-alkyl, —C(O)-alkenyl, —C(O)-heteroalkyl, —C(O)-heteroaryl, —C(O)-alkoxyalkyl, —C(O)—O-heteroalkyl, —C(O)—O-heteroaryl, —C(O)—O— alkyl, —C(O)—O-alkenyl, and —C(O)—O-alkoxyalkyl; $R^5$, $R^6$ and $R^7$ are each independently selected from hydrogen, alkyl, —C(O)-alkyl, —C(O)—O-alkyl, —C(O)—O-alkenyl, —C(O)— alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl; provided that when $R^4$ is —C(O)-alkyl, —C(O)-alkenyl, —C(O)-heteroalkyl, —C(O)-heteroaryl, or —C(O)-alkoxyalkyl, $R^2$ is —C(O)-alkyl, —C(O)—O-alkyl, —C(O)-alkenyl, —C(O)—O-alkenyl, —C(O)-alkoxyalkyl, —C(O)—O-alkoxyalkyl, —C(O)— heteroalkyl, —C(O)-heteroaryl, —C(O)—O-heteroalkyl, or —C(O)—O-heteroaryl.

In certain embodiments, $R^2$ and $R^{1e}$ together form a 5 to 8-membered ring. In certain embodiments, $R^2$ and $R^{1e}$ together form a 5-membered ring. In certain embodiments, $R^2$ and $R^{1e}$ together form a 6-membered ring. In certain embodiments, $R^2$ and $R^{1e}$ together form a 7-membered ring. In certain embodiments, $R^2$ and $R^{1e}$ together form an 8-membered ring.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is hydrogen; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from C(O)—O-alkyl and —C(O)—O-alkenyl; $R^8$ is selected from hydrogen and alkyl, and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is hydrogen; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from C(O)—O-alkyl and —C(O)—O-alkenyl; and $R^9$ is selected from alkyl, aryl, and heteroaryl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is selected from —C(O)-alkenyl and —C(O)—O-alkenyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkenyl and —C(O)—O-alkenyl; $R^8$ is selected from hydrogen and alkyl; and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is selected from —C(O)-alkenyl and —C(O)—O-alkenyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkenyl and —C(O)—O-alkenyl; and $R^9$ is selected from alkyl, aryl, and heteroaryl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is —C(O)-alkyl or —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl and —C(O)—O-alkyl; $R^8$ is selected from hydrogen and alkyl; and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is —C(O)-alkyl or —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl and —C(O)—O-alkyl; and $R^9$ is selected from alkyl, aryl, and heteroaryl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is hydrogen; $R^{3a}$, $R^{3b}$, $R^{3d}$ and $R^{3e}$ are independently selected from hydrogen, halogen, nitro, alkyl, cyano, haloalkyl, $SO_2$—$R^9$, and $OR^4$; $R^4$ is selected from C(O)-alkyl and —C(O)-alkenyl; $R^8$ is selected from hydrogen and alkyl; and $R^9$ is selected from alkyl, aryl, and heteroaryl.

Representative compounds of formula (II) include, but are not limited to:

4-chloro-2-((2-chloro-4-nitrophenyl)carbamoyl)phenyl octyl carbonate;

4-chloro-2-((2-chloro-4-(trifluoromethyl)phenyl)carbamoyl)phenyl ethyl carbonate;

octyl (5-chloro-2-(((octyloxy)carbonyl)oxy)benzoyl)(2-chloro-4-nitrophenyl)carbamate; and
4-chloro-2-((2-chloro-4-nitrophenyl)(heptanoyl)carbamoyl)phenyl heptanoate;
or a pharmaceutically acceptable salt thereof.

In another aspect, disclosed is a compound of formula (III),

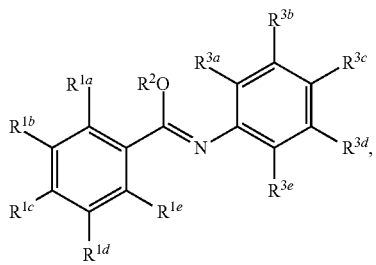

(III)

or a pharmaceutically acceptable salt thereof; wherein one of $R^{1a}$, $R^{1b}$, $R^{1c}$, $R^{1d}$ and $R^{1e}$ is $OR^4$ or $NR^8$—$SO_2$—$R^9$, and the remaining are independently selected from hydrogen, halogen, nitro, alkyl, cyano, haloalkyl, alkoxyalkyl, heteroalkyl, alkenyl, alkynyl, heterocycle, carboxyl, heterocyclealkyl, OH, alkoxy, $OR^4$, $SR^5$, $NR^6R^7$, and $NR^8$—$SO_2$—$R^9$; or $R^{1b}$ and $R^{1c}$ together form a six-membered aromatic ring; $R^2$ is selected from —C(O)-alkyl, —C(O)—O-alkyl, —C(O)— alkenyl, —C(O)—O-alkenyl, —C(O)-alkoxyalkyl, —C(O)—O-alkoxyalkyl, —C(O)-heteroalkyl, —C(O)-heteroaryl, —C(O)—O-heteroalkyl, and —C(O)—O-heteroaryl; $R^{3a}$, $R^{3b}$, $R^{3c}$, $R^{3d}$ and $R^{3e}$ are independently selected from hydrogen, halogen, nitro, alkyl, cyano, haloalkyl, alkoxyalkyl, heteroalkyl, alkenyl, alkynyl, heterocycle, carboxyl, heterocyclealkyl, alkoxy, OH, $OR^4$, $SR^5$, $NR^6R^7$, $SO_2$—$R^9$, and $NR^8$—$SO_2$—$R^9$; $R^4$ is selected from —C(O)-alkyl, —C(O)-alkenyl, —C(O)— heteroalkyl, —C(O)-heteroaryl, —C(O)-alkoxyalkyl, —C(O)—O-heteroalkyl, —C(O)—O-heteroaryl, C(O)—O-alkyl, —C(O)—O-alkenyl, and —C(O)—O-alkoxyalkyl; $R^5$, $R^6$ and $R^7$ are each independently selected from hydrogen, alkyl, —C(O)-alkyl, —C(O)—O-alkyl, —C(O)—O-alkenyl, —C(O)-alkoxyalkyl, —C(O)—NH-alkyl, —C(O)-heterocycle, alkenyl, alkynyl, and heteroalkyl; $R^8$ is selected from hydrogen and alkyl; and $R^9$ is selected from hydrogen, alkyl, aryl, heteroaryl, arylalkyl, heterocycle and heteroarylalkyl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is —C(O)-alkyl, —C(O)-alkenyl, —C(O)—O-alkenyl or —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl, —C(O)-alkenyl, —C(O)—O-alkenyl or —C(O)—O-alkyl; $R^8$ is selected from hydrogen and alkyl; and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is —C(O)-alkyl, —C(O)-alkenyl, —C(O)—O-alkenyl or —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl, —C(O)-alkenyl, —C(O)—O-alkenyl or —C(O)—O— alkyl; and $R^9$ is selected from alkyl, aryl, and heteroaryl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is selected from —C(O)-alkyl and —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl and —C(O)—O-alkyl; $R^8$ is selected from hydrogen and alkyl; and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is selected from —C(O)-alkyl and —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl and —C(O)—O-alkyl; and $R^9$ is selected from alkyl, aryl, and heteroaryl.

In certain embodiments, $R^{1a}$ is $OR^4$ or $NR^8$—$SO_2$—$R^9$; $R^{1b}$, $R^{1c}$ and $R^{1e}$ are hydrogen; $R^{1d}$ is halogen; $R^2$ is selected from —C(O)-alkyl and —C(O)—O-alkyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkenyl and —C(O)—O-alkenyl; $R^8$ is selected from hydrogen and alkyl; and $R^9$ is selected from alkyl, aryl, and heteroaryl.

In certain embodiments, $R^{1a}$ is $OR^4$; $R^{1b}$, $R^{1c}$ and $R^{1e}$ are hydrogen; $R^{1d}$ is halogen; $R^2$ is selected from —C(O)-alkenyl and —C(O)—O-alkenyl; $R^{3a}$, $R^{3b}$, $R^{3c}$, $R^{3d}$ and $R^{3e}$ are independently selected from hydrogen, halogen, nitro, alkyl, cyano, haloalkyl, $SO_2$—$R^9$, and $OR^4$; $R^4$ is selected from —C(O)-alkyl and —C(O)—O-alkyl; and $R^9$ is selected from alkyl, aryl, and heteroaryl.

Representative compounds of formula (III) include, but are not limited to:
5-chloro-N-(2-chloro-4-nitrophenyl)-2-(heptanoyloxy)benzimidic heptanoic anhydride; and
5-chloro-N-(2-chloro-4-nitrophenyl)-2-(((octyloxy)carbonyl)oxy)benzimidic (octyl carbonic) anhydride,
or a pharmaceutically acceptable salt thereof.

In another aspect, disclosed are the following compounds:
4-chloro-2-((2-chloro-4-(trifluoromethyl)phenyl)carbamoyl)phenyl acetate;
4-chloro-2-((2-chloro-4-nitrophenyl)carbamoyl)phenyl octanoate;
4-chloro-2-((2-chloro-4-nitrophenyl)carbamoyl)phenyl heptanoate;
4-chloro-2-((2-chloro-4-nitrophenyl)carbamoyl)phenyl isobutyrate;
tert-butyl (4-chloro-2-((2-chloro-4-nitrophenyl)carbamoyl)phenyl) succinate;
4-chloro-2-((2-chloro-4-nitrophenyl)carbamoyl)phenyl 2-propylpentanoate;
4-chloro-2-((2-chloro-4-nitrophenyl)carbamoyl)phenyl 6-(2,5-dioxo-2,5-dihydro-1H-pyrrol-1-yl)hexanoate;
4-chloro-2-((2-chloro-4-nitrophenyl)carbamoyl)phenyl oleate;
4-chloro-2-((2-chloro-4-nitrophenyl)carbamoyl)phenyl (9Z,12Z)-octadeca-9,12-dienoate;
4-chloro-2-((2-chloro-4-nitrophenyl)carbamoyl)phenyl morpholine-4-carboxylate;
5-chloro-2-hydroxy-N-phenylbenzamide;
N-(4-acetylphenyl)-5-chloro-2-hydroxybenzamide;
N-(4-carbamoylphenyl)-5-chloro-2-hydroxybenzamide;
N-(4-benzoylphenyl)-5-chloro-2-hydroxybenzamide;
5-chloro-2-hydroxy-N-(4-(phenylcarbamoyl)phenyl)benzamide;
5-chloro-N-(2-chloro-4-(trifluoromethyl)phenyl)-2-hydroxybenzamide;
5-chloro-2-hydroxy-N-(4-(trifluoromethyl)phenyl)benzamide;
5-chloro-2-hydroxy-N-(3-(trifluoromethyl)phenyl)benzamide;

5-chloro-N-(2-fluoro-4-(trifluoromethyl)phenyl)-2-hydroxybenzamide;
5-chloro-N-(4-chlorophenyl)-2-hydroxybenzamide;
5-chloro-N-(3-chlorophenyl)-2-hydroxybenzamide;
5-chloro-N-(2-chlorophenyl)-2-hydroxybenzamide;
5-chloro-N-(2,4-dichlorophenyl)-2-hydroxybenzamide;
5-chloro-N-(2,5-dichlorophenyl)-2-hydroxybenzamide;
5-chloro-N-(3,5-dichlorophenyl)-2-hydroxybenzamide;
5-chloro-N-(3,4-dichlorophenyl)-2-hydroxybenzamide;
5-chloro-N-(2,6-dichlorophenyl)-2-hydroxybenzamide;
5-chloro-N-(4-fluorophenyl)-2-hydroxybenzamide;
5-chloro-N-(2,4-difluorophenyl)-2-hydroxybenzamide;
5-chloro-N-(2,6-difluorophenyl)-2-hydroxybenzamide;
5-chloro-N-(2-chloro-4-fluorophenyl)-2-hydroxybenzamide;
5-chloro-N-(3-chloro-4-fluorophenyl)-2-hydroxybenzamide;
5-chloro-2-hydroxy-N-methyl-N-(4-(trifluoromethyl)phenyl)benzamide;
5-chloro-2-hydroxy-N-(4-(trifluoromethyl)benzyl)benzamide;
5-chloro-2-hydroxy-N-(4-(trifluoromethyl)benzoyl)benzamide;
6-chloro-3-(2-chloro-4-(trifluoromethyl)phenyl)-2H-benzo[e][1,3]oxazine-2,4(3H)-dione;
6-chloro-3-(4-(trifluoromethyl)phenyl)-2H-benzo[e][1,3]oxazine-2,4(3H)-dione;
6-chloro-3-(2-chloro-4-nitrophenyl)-2H-benzo[e][1,3]oxazine-2,4(3H)-dione;
2-((4-methylphenyl)sulfonamido)-N-(4-nitrophenyl)benzamide;
5-bromo-N-(4-bromophenyl)-2-hydroxybenzamide;
N-(2-chloro-4-nitrophenyl)-4-hydroxy-[1,1'-biphenyl]-3-carboxamide;
5-chloro-2-hydroxy-N-(2-methyl-4-nitrophenyl)benzamide;
N-(2-chloro-4-nitrophenyl)-2',4'-difluoro-4-hydroxy-[1,1'-biphenyl]-3-carboxamide;
N-(2-chloro-4-(trifluoromethyl)phenyl)-2-hydroxy-1-naphthamide;
N-(2-chloro-4-(trifluoromethyl)phenyl)-3-hydroxy-2-naphthamide;
N-(2-chloro-4-(trifluoromethyl)phenyl)-1-hydroxy-2-naphthamide;
N-(4-(benzyloxy)-3-chlorophenyl)-5-chloro-2-hydroxybenzamide;
N-(2-chloro-4-nitrophenyl)-2-hydroxy-4,5-dimethoxybenzamide;
N-(4-(benzyloxy)-3-chlorophenyl)-2-hydroxy-4,5-dimethoxybenzamide;
N-(2-bromo-4-(trifluoromethyl)phenyl)-5-chloro-2-hydroxybenzamide;
5-bromo-2-((4-methylphenyl)sulfonamido)-N-(4-(trifluoromethyl)phenyl)benzamide;
5-chloro-2-hydroxy-N-(4-nitro-2-((10,17,24-trioxo-28-(2-oxohexahydro-1H-thieno[3,4-d]imidazol-4-yl)-3,6-dioxa-9,16,23-triazaoctacosyl)oxy)phenyl)benzamide;
4-hydroxy-N-(4-(trifluoromethyl)phenyl)quinoline-3-carboxamide;
N-(2-(allyloxy)-4-nitrophenyl)-5-chloro-2-hydroxybenzamide;
5-chloro-N-(2-chloro-4-nitrophenyl)-2-((4-methylphenyl)sulfonamido)benzamide;
5-chloro-2-hydroxy-N-(4-nitro-2-(2-oxoethoxy)phenyl)benzamide;
5-chloro-N-(3-fluoro-4-nitrophenyl)-2-hydroxybenzamide;
5-chloro-2-hydroxy-N-(4-nitro-2-(prop-2-yn-1-yloxy)phenyl)benzamide;
5-chloro-2-hydroxy-N-(3-morpholino-4-nitrophenyl)benzamide;
5-chloro-2-hydroxy-N-(3-methoxy-4-nitrophenyl)benzamide;
2-((2-(allyloxy)-4-nitrophenyl)carbamoyl)-4-chlorophenyl acetate;
4-chloro-2-((2-chloro-4-nitrophenyl)carbamoyl)phenyl stearate;
5-chloro-N-(3-chloro-4-nitrophenyl)-2-hydroxybenzamide;
N-(4-azido-2-(prop-2-yn-1-yloxy)phenyl)-5-chloro-2-hydroxybenzamide;
5-chloro-N-(3-chloro-4-(trifluoromethyl)phenyl)-2-hydroxybenzamide;
5-chloro-N-(2-(hex-5-yn-1-yloxy)-4-nitrophenyl)-2-hydroxybenzamide;
5-chloro-N-(2-chloro-4-nitrophenyl)-2-(methylsulfonamido)benzamide;
5-chloro-N-(2-chloro-4-(trifluoromethyl)phenyl)-2-(methylsulfonamido)benzamide;
N-(2-chloro-4-nitrophenyl)-2-hydroxy-4-methoxybenzamide;
5-chloro-N-(2-chloro-4-nitrophenyl)-2-hydroxy-4-methoxybenzamide;
5-chloro-N-(2-chloro-4-fluorophenyl)-2-hydroxy-4-methoxybenzamide;
5-chloro-N-(3-chlorophenyl)-2-hydroxy-4-methoxybenzamide; and
6-chloro-3-(2-fluoro-4-(trifluoromethyl)phenyl)-2H-benzo[e][1,3]oxazine-2,4(3H)-dione, or a pharmaceutically acceptable salt thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Fumiss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present invention also includes an isotopically-labeled compound, which is identical to those recited in the present disclosure, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of the present disclosure are $^{11}C$, $^{13}N$, $^{15}O$, and $^{18}F$. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

A. Inhibition of Wnt Signaling

The disclosed compounds may act or function as inhibitors of the Wnt/Frizzled signaling pathway. The compounds may promote the anti-proliferation of cancer cells even in the presence of Wnt/Frizzled signaling dysfunction.

Compounds of the present disclosure can inhibit Wnt-3A-stimulated signaling with an $IC_{50}$ ranging from about 1 nM to about 30 µM. The compounds may have an $IC_{50}$ of about 30 µM, about 29 µM, about 28 µM, about 27 µM, about 26 µM, about 25 µM, about 24 µM, about 23 µM, about 22 µM, about 21 µM, about 20 µM, about 19 µM, about 18 µM, about 17 µM, about 16 µM, about 15 µM, about 14 µM, about 13 µM, about 12 µM, about 11 µM, about 10 µM, about 9 µM, about 8 µM, about 7 µM, about 6 µM, about 5 µM, about 4 µM, about 3 µM, about 2 µM, about 1 µM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of the present disclosure can inhibit Wnt-3A-stimulated signaling with an $IC_{50}$ of less than 30 µM, less than 29 µM, less than 28 µM, less than 27 µM, less than 26 µM, less than 25 µM, less than 24 µM, less than 23 µM, less than 22 µM, less than 21 µM, less than 20 µM, less than 19 µM, less than 18 µM, less than 17 µM, less than 16 µM, less than 15 µM, less than 14 µM, less than 13 µM, less than 12 µM, less than 11 µM, less than 10 µM, less than 9 µM, less than 8 µM, less than 7 µM, less than 6 µM, less than 5 µM, less than 4 µM, less than 3 µM, less than 2 µM, less than 1 µM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

1. Compound of Formula (I)

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^{1a}$, $R^{1b}$, $R^{1c}$, $R^{1d}$, $R^{1e}$, $R^{2}$, $R^{3a}$, $R^{3b}$, $R^{3c}$, $R^{3d}$ and $R^{3e}$ have the meanings as set forth in the Summary of the Invention section unless otherwise noted, can be synthesized as shown in Scheme 1.

Scheme 1. Synthesis of the compound of formula (I)

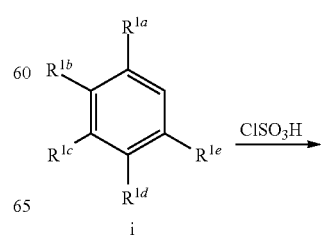

i

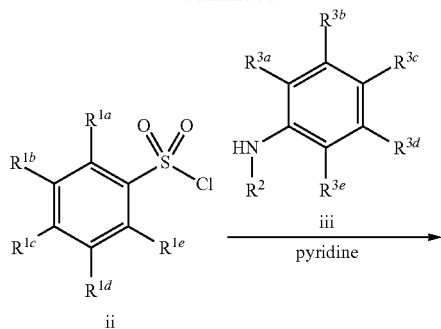

(I)

As shown in Scheme 1, intermediate ii, wherein $R^{1a}$, $R^{1b}$, $R^{1c}$, $R^{1d}$ and $R^{1e}$ are as defined in the Summary of the Invention, can be prepared from the substituted benzene, i, and chlorosulfonic acid. Treatment of ii with aniline iii, wherein $R^{3a}$, $R^{3b}$, $R^{3c}$, $R^{3d}$ and $R^{3e}$ are as defined in the Summary of the Invention, in the presence of pyridine can provide the compound of formula (I).

2. Compound of Formula (II) and (III)

Compounds of formula (II) and (III) may be prepared by synthetic processes or by metabolic processes. Preparation of the compounds by metabolic processes includes those occurring in the human or animal body (in vivo) or processes occurring in vitro.

Compounds of formula (II) or (III), wherein the groups $R^{1a}$, $R^{1b}$, $R^{1c}$, $R^{1d}$, $R^{1e}$, $R^2$, $R^{3a}$, $R^{3b}$, $R^{3c}$, $R^{3d}$ and $R^{3e}$ have the meanings as set forth in the Summary of the Invention section unless otherwise noted, can be synthesized as shown in Schemes 2-4.

Scheme 2. Synthesis of the compound of formula (II)

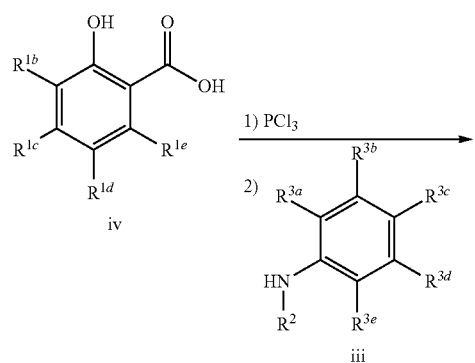

In scheme 2, benzoic acid iv, wherein $R^{1a}$ is OH and represents the substituent that will be $OR^4$, and $R^{1b}$, $R^{1c}$, $R^{1d}$ and $R^{1e}$ are as defined in the Summary of the Invention, can be transformed to intermediate v by conversion to the acid chloride followed by addition of aniline iii. The hydroxyl group of intermediate v can be converted to the corresponding carbonate to yield the compound of formula (II) wherein $R^{1a}$ is $OR^4$ and $R^4$ is C(O)O-alkyl or C(O)O-alkenyl. In the foregoing scheme, $R^4$ is represented by $C(O)OR^{10}$.

Scheme 3. Synthesis of the compound of formula (II) or (III)

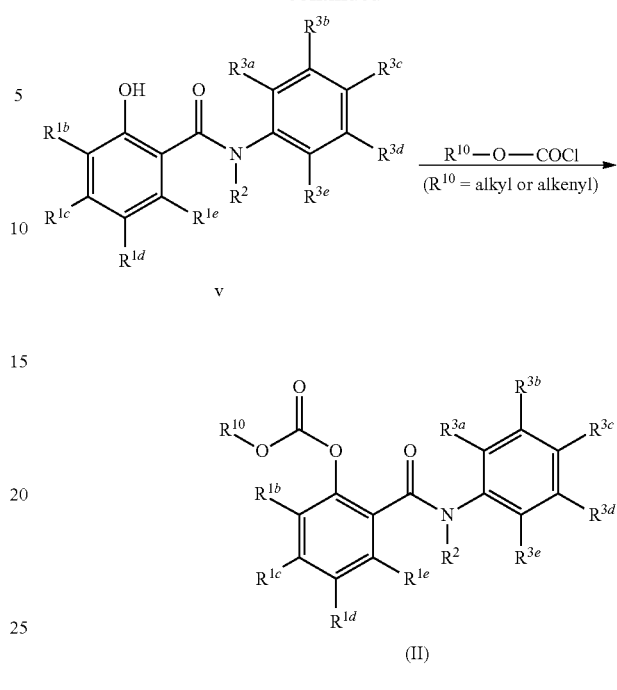

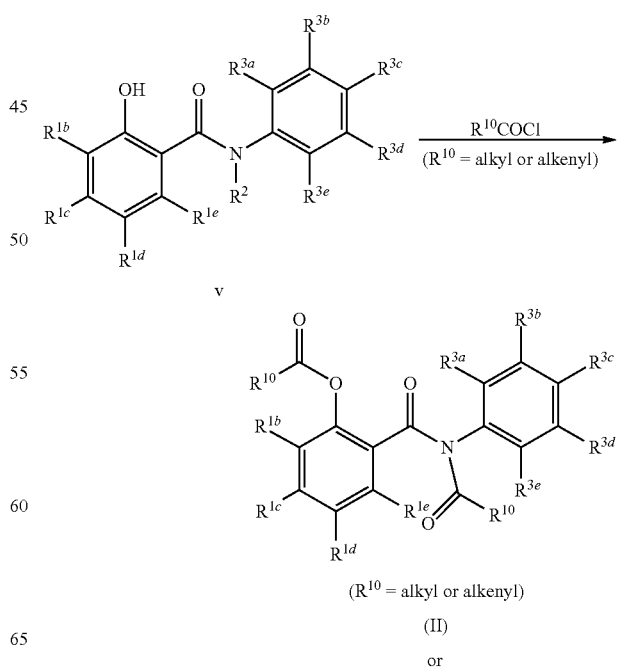

($R^{10}$ = alkyl or alkenyl)

(II)

or

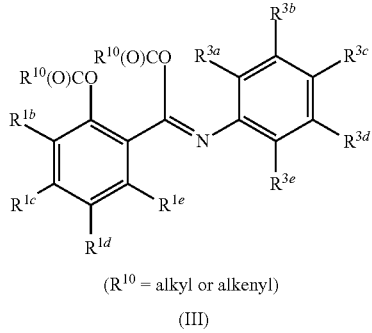

(R$^{10}$ = alkyl or alkenyl)

(III)

In scheme 3, compound v, wherein R$^2$ is H, can be converted to the compound of formula (II) or formula (III), wherein R$^2$ is C(O)-alkyl or C(O)-alkenyl, by the addition of two equivalents of the appropriate acid chloride. In the foregoing scheme, R$^4$ is represented by C(O)OR$^{10}$ and R$^2$ is represented by C(O)R$^{10}$.

Scheme 4. Synthesis of the compound of formula (II) or (III)

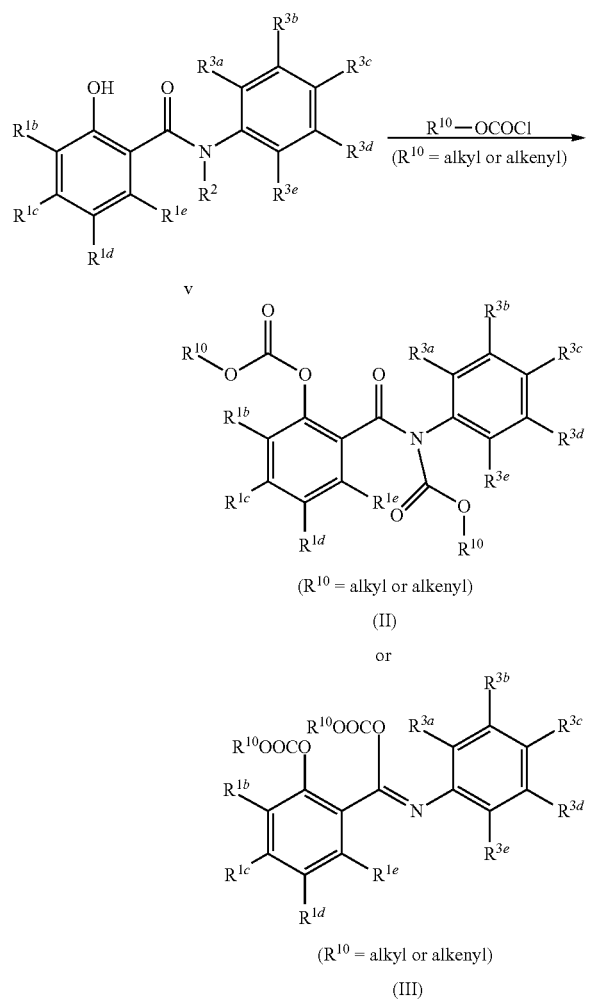

Likewise in Scheme 4, compound v, wherein R$^2$ is H, can be converted to the compound of formula (II) or formula (III), wherein R$^2$ is C(O)O-alkyl or C(O)O-alkenyl, by the addition of two equivalents of the appropriate alkyl or alkenyl chloroformate (Scheme 4). In the foregoing scheme, R$^4$ is represented by C(O)OR$^{10}$ and R$^2$ is represented by C(O)OR$^{10}$ Employing analogous synthetic methods and the syntheses provided in the Examples, the remaining compounds of the disclosure may be obtained.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

4. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound, and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The compounds and processes of the invention will be better understood by reference to the following examples, which are intended as an illustration of and not a limitation upon the scope of the invention.

5. EXAMPLES

Example 1. Anilide Synthesis

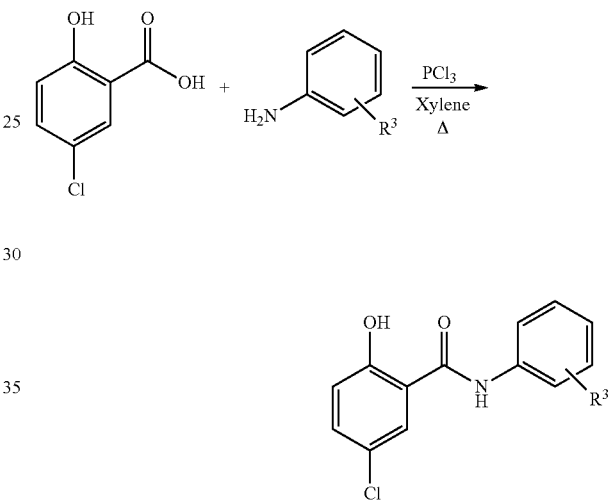

General Method:

To a 100 mL flask equipped with a reflux condenser was added 5-chloro-2-hydroxybenzoic acid (1 equiv.), the aniline derivative (1 equiv.), and dry xylenes (stored over 3A molecular sieves, 40 mL per gram of 5-chloro-2-hydroxybenzoic acid) under an atmosphere of argon. The mixture was heated to reflux, and $PCl_3$ (0.4 equiv.) was added rapidly via syringe. The mixture was heated at reflux for 1 hour and cooled to room temperature. Water (40 mL per gram of 5-chloro-2-hydroxybenzoic acid) was added and the resultant heterogeneous mixture stirred rapidly for 1 hour. Saturated sodium bicarbonate was added to a final pH of 3-4, and the mixture stirred rapidly overnight. The solids were filtered and washed sequentially with water, toluene and hexane. Samples were analyzed by NMR, HPLC/mass spectrometry and TLC. Purification by crystallization or column chromatography on silica gel was performed when purity was less than 95% by LC. HPLC/MS was accomplished using an Agilent spectrometer-6310 Ion trap. Mass ions (m/z) detected in positive ionization mode are M+; in negative ionization mode, mass ions (m/z) are M−.

The following compounds were made employing analogous synthetic procedures:

| No. | Aniline Starting Material | Compound | MS (m/z) |
| --- | --- | --- | --- |
| 1 | aniline | 5-chloro-2-hydroxy-N-phenylbenzamide | (ESI+) = 248, 250 (M + 1) |
| 2 | 4-nitroaniline | 5-chloro-2-hydroxy-N-(4-nitrophenyl)benzamide | (ESI−) = 291, 293 (M − 1) |
| 3 | 4-aminoacetophenone | N-(4-acetylphenyl)-5-chloro-2-hydroxybenzamide | (ESI+) = 290, 292 (M + 1) (ESI−) = 288, 289 (M − 1) |
| 4 | 4-aminobenzamide | N-(4-carbamoylphenyl)-5-chloro-2-hydroxybenzamide | (ESI−) = 289, 291 (M − 1) |
| 5 | 2-chloro-4-(methylsulfonyl)aniline | 5-chloro-N-(2-chloro-4-(methylsulfonyl)phenyl)-2-hydroxybenzamide | (ESI+) = 359.9855 (M + 1) |

-continued

| No. | Aniline Starting Material | Compound | MS (m/z) |
|---|---|---|---|
| 6 | 4-aminobenzophenone | N-(4-benzoylphenyl)-5-chloro-2-hydroxybenzamide | (ESI−) = 350 (M − 1) |
| 7 | 2-chloro-4-(trifluoromethyl)aniline | 5-chloro-N-(2-chloro-4-(trifluoromethyl)phenyl)-2-hydroxybenzamide | (ESI−) = 348, 350 (M − 1) |
| 8 | 4-(trifluoromethyl)aniline | 5-chloro-2-hydroxy-N-(4-(trifluoromethyl)phenyl)benzamide | (ESI−) = 314, 316 (M − 1) |
| 9 | 3-(trifluoromethyl)aniline | 5-chloro-2-hydroxy-N-(3-(trifluoromethyl)phenyl)benzamide | (ESI−) = 314, 316 (M − 1) |
| 10 | 2-fluoro-4-(trifluoromethyl)aniline | 5-chloro-N-(2-fluoro-4-(trifluoromethyl)phenyl)-2-hydroxybenzamide | (ESI−) = 332 (M − 1) |

| No. | Aniline Starting Material | Compound | MS (m/z) |
|---|---|---|---|
| 11 | 4-chloroaniline | 5-chloro-N-(4-chlorophenyl)-2-hydroxybenzamide | (ESI+) = 282, 284 (M + 1) |
| 12 | 3-chloroaniline | 5-chloro-N-(3-chlorophenyl)-2-hydroxybenzamide | (ESI−) = 280, 282 (M − 1) |
| 13 | 2-chloroaniline | 5-chloro-N-(2-chlorophenyl)-2-hydroxybenzamide | (ESI−) = 280, 282 (M − 1) |
| 14 | 2,4-dichloroaniline | 5-chloro-N-(2,4-dichlorophenyl)-2-hydroxybenzamide | (ESI−) = 314, 316, 318 (M − 1) |
| 15 | 2,5-dichloroaniline | 5-chloro-N-(2,5-dichlorophenyl)-2-hydroxybenzamide; | (ESI−) = 314, 316 (M − 1) |
| 16 | 3,5-dichloroaniline | 5-chloro-N-(3,5-dichlorophenyl)-2-hydroxybenzamide | (ESI−) = 314, 316 (M − 1) |

-continued

| No. | Aniline Starting Material | Compound | MS (m/z) |
|---|---|---|---|
| 17 | 3,4-dichloroaniline | 5-chloro-N-(3,4-dichlorophenyl)-2-hydroxybenzamide | (ESI−) = 314, 316, 318 (M − 1) |
| 18 | 2,6-dichloroaniline | 5-chloro-N-(2,6-dichlorophenyl)-2-hydroxybenzamide | (ESI−) = 314, 316, 318 (M − 1) |
| 19 | 4-fluoroaniline | 5-chloro-N-(4-fluorophenyl)-2-hydroxybenzamide | (ESI+) = 266, 268 (M + 1) |
| 20 | 2,4-difluoroaniline | 5-chloro-N-(2,4-difluorophenyl)-2-hydroxybenzamide | (ESI−) = 282 (M − 1) |
| 21 | 2,6-difluoroaniline | 5-chloro-N-(2,6-difluorophenyl)-2-hydroxybenzamide | (ESI−) = 282 (M − 1) |
| 22 | 2-chloro-4-fluoroaniline | 5-chloro-N-(2-chloro-4-fluorophenyl)-2-hydroxybenzamide | (ESI−) = 298, 300 (M − 1) |

-continued

| No. | Aniline Starting Material | Compound | MS (m/z) |
|---|---|---|---|
| 23 | 4-fluoro-3-chloroaniline | 5-chloro-N-(3-chloro-4-fluorophenyl)-2-hydroxybenzamide | (ESI−) = 298, 300 (M − 1) |
| 24 | N-methyl-4-(trifluoromethyl)aniline | 5-chloro-2-hydroxy-N-methyl-N-(4-(trifluoromethyl)phenyl)benzamide | (ESI−) = 328 (M − 1) |
| 25 | 4-(trifluoromethyl)benzylamine | 5-chloro-2-hydroxy-N-(4-(trifluoromethyl)benzyl)benzamide | (ESI−) = 328, 330 (M − 1) |
| 26 | 2-methyl-4-nitroaniline | 5-chloro-2-hydroxy-N-(2-methyl-4-nitrophenyl)benzamide | (ESI−) = 305, 307 (M − 1) |
| 27 | 4-(benzyloxy)-3-chloroaniline | N-(4-(benzyloxy)-3-chlorophenyl)-5-chloro-2-hydroxybenzamide | (ESI−) = 386 (M − 1) |

-continued

| No. | Aniline Starting Material | Compound | MS (m/z) |
|---|---|---|---|
| 28 |  | 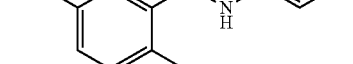 N-(2-bromo-4-(trifluoromethyl)phenyl)-5-chloro-2-hydroxybenzamide | (ESI−) = 392, 394 (M − 1) |
| 29 |  | 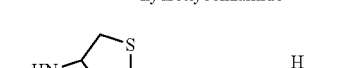 5-chloro-2-hydroxy-N-(4-nitro-2-((10,17,24-trioxo-28-(2-oxohexahydro-1H-thieno[3,4-d]imidazol-4-yl)-3,6-dioxa-9,16,23-triazaoctacosyl)oxy)phenyl)benzamide | (ESI−) = 890, 892 (M − 1) |
| 30 | 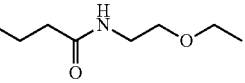 | 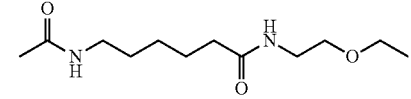 N-(2-(allyloxy)-4-nitrophenyl)-5-chloro-2-hydroxybenzamide | (ESI+) = 349, 351 (M + 1) |
| 31 |  | 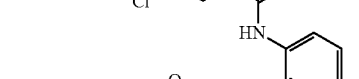 5-chloro-2-hydroxy-N-(4-nitro-2-(2-oxoethoxy)phenyl)benzamide | (ESI+) = 351 (M + 1) |

-continued

| No. | Aniline Starting Material | Compound | MS (m/z) |
|---|---|---|---|
| 32 | 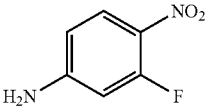 | 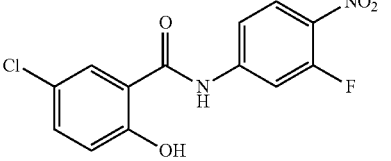<br>5-chloro-N-(3-fluoro-4-nitrophenyl)-2-hydroxybenzamide | (ESI−) = 311, 313 (M − 1) |
| 33 | 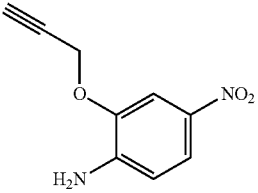 | 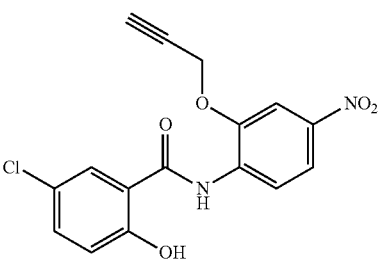 [SMILES: C#CCOc1cc([N+](=O)[O-])ccc1NC(=O)c1cc(Cl)ccc1O]<br>5-chloro-2-hydroxy-N-(4-nitro-2-(prop-2-yn-1-yloxy)phenyl)benzamide | (ESI−) = 345, 347 (M − 1) |
| 34 | 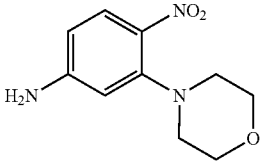 [SMILES: Nc1ccc([N+](=O)[O-])c(N2CCOCC2)c1] | 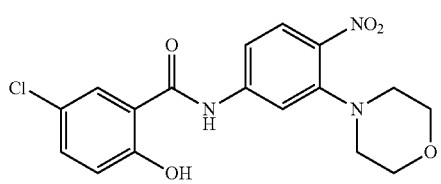 [SMILES: O=C(Nc1ccc([N+](=O)[O-])c(N2CCOCC2)c1)c1cc(Cl)ccc1O]<br>5-chloro-2-hydroxy-N-(3-morpholino-4-nitrophenyl)benzamide | (ESI−) = 376, 378 (M − 1) |
| 35 | 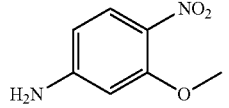 | 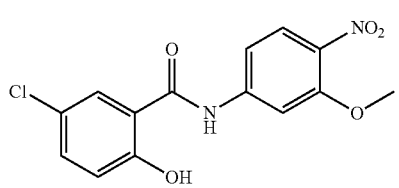 [SMILES: COc1cc(NC(=O)c2cc(Cl)ccc2O)ccc1[N+](=O)[O-]]<br>5-chloro-2-hydroxy-N-(3-methoxy-4-nitrophenyl)benzamide | (ESI−) = 321, 323 (M − 1) |
| 36 | 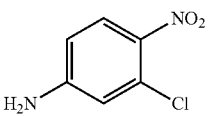 | 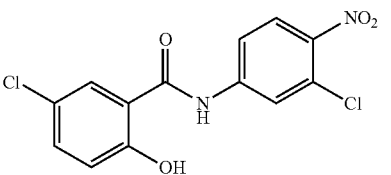 [SMILES: O=C(Nc1ccc([N+](=O)[O-])c(Cl)c1)c1cc(Cl)ccc1O]<br>5-chloro-N-(3-chloro-4-nitrophenyl)-2-hydroxybenzamide | (ESI−) = 325, 327 (M − 1) |

-continued
| No. | Aniline Starting Material | Compound | MS (m/z) |
|---|---|---|---|
| 37 | 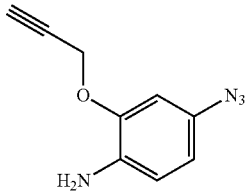 | 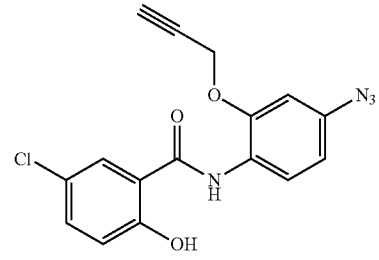 [SMILES: C#CCOc1cc(N=[N+]=[N-])ccc1NC(=O)c1cc(Cl)ccc1O]<br>N-(4-azido-2-(prop-2-yn-1-yloxy)phenyl)-5-chloro-2-hydroxybenzamide | (ESI+) = 343, 345 (M + 1) |
| 38 | 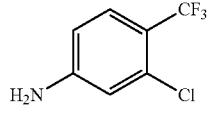 | 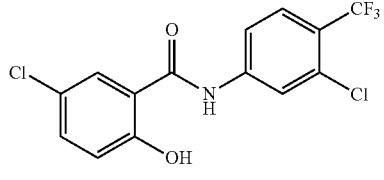 [SMILES: O=C(Nc1ccc(C(F)(F)F)c(Cl)c1)c1cc(Cl)ccc1O]<br>5-chloro-N-(3-chloro-4-(trifluoromethyl)phenyl)-2-hydroxybenzamide | (ESI−) = 348, 350 (M − 1) |
| 39 | 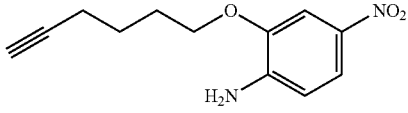 | 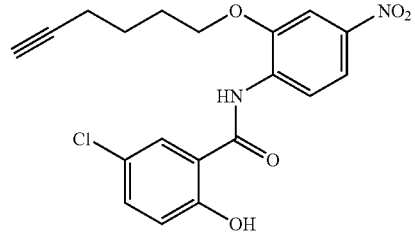 [SMILES: C#CCCCCOc1cc([N+](=O)[O-])ccc1NC(=O)c1cc(Cl)ccc1O]<br>5-chloro-N-(2-(hex-5-yn-1-yloxy)-4-nitrophenyl)-2-hydroxybenzamide | (ESI+) = 389, 391 (M + 1) |
| 40 | 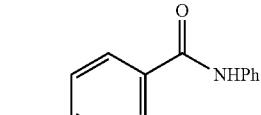 | 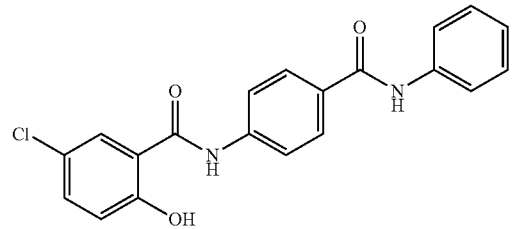 [SMILES: O=C(Nc1ccccc1)c1ccc(NC(=O)c2cc(Cl)ccc2O)cc1]<br>5-chloro-2-hydroxy-N-(4-(phenylcarbamoyl)phenyl)benzamide | (ESI−) = 350 (M − 1) |

Example 2. Additional Anilides Synthesis

In analogous fashion to the procedure of Example 1 used to construct compounds 1-40, the following compounds were synthesized employing the indicated starting materials.

| No | Carboxylic acid | Aniline | Compound | MS (m/z) |
|---|---|---|---|---|
| 41 | | | N-(2-chloro-4-nitrophenyl)-4-hydroxy-[1,1'-biphenyl]-3-carboxamide | (ESI−) = 367 (M − 1) |
| 42 | | | N-(2-chloro-4-nitrophenyl)-2',4'-difluoro-4-hydroxy-[1,1'-biphenyl]-3-carboxamide | (ESI−) = 403 (M − 1) |
| 43 | | | N-(2-chloro-4-(trifluoromethyl)phenyl)-2-hydroxy-1-naphthamide | (ESI−) = 364, 366 (M − 1) |
| 44 | | | N-(2-chloro-4-(trifluoromethyl)phenyl)-3-hydroxy-2-naphthamide | (ESI−) = 364, 366 (M − 1) |
| 45 | | | N-(2-chloro-4-(trifluoromethyl)phenyl)-1-hydroxy-2-naphthamide | (ESI−) = 364, 366 (M − 1) |

-continued

| No | Carboxylic acid | Aniline | Compound | MS (m/z) |
|---|---|---|---|---|
| 46 | 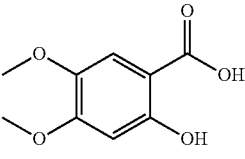 | 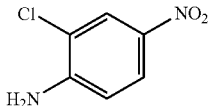 | 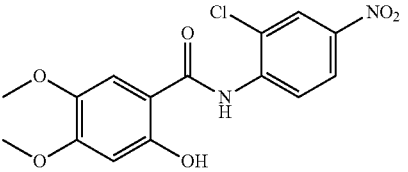 [SMILES: COc1cc(O)c(C(=O)Nc2ccc([N+](=O)[O-])cc2Cl)cc1OC] N-(2-chloro-4-nitrophenyl)-2-hydroxy-4,5-dimethoxybenzamide | (ESI−) = 351 (M − 1) |
| 47 | 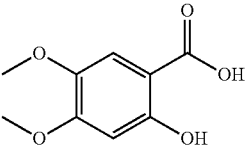 | 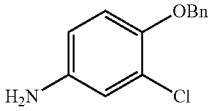 | 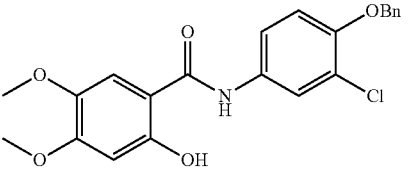 [SMILES: COc1cc(O)c(C(=O)Nc2ccc(OCc3ccccc3)c(Cl)c2)cc1OC] N-(4-(benzyloxy)-3-chlorophenyl)-2-hydroxy-4,5-dimethoxybenzamide | (ESI−) = 412, 414 (M − 1) |
| 48 | 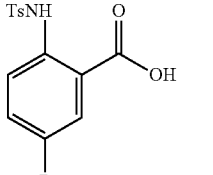 | 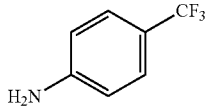 | 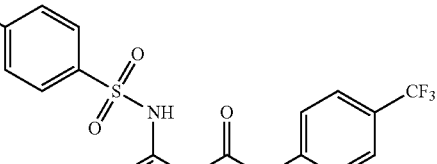 5-bromo-2-((4-methylphenyl)sulfonamido)-N-(4-(trifluoromethyl)phenyl)benzamide | (ESI−) = 511, 513 (M − 1) |
| 49 | 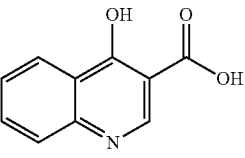 [SMILES: O=C(O)c1cnc2ccccc2c1O] | 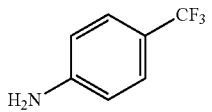 | 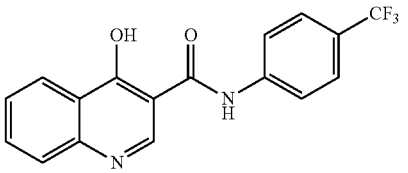 [SMILES: O=C(Nc1ccc(C(F)(F)F)cc1)c1cnc2ccccc2c1O] 4-hydroxy-N-(4-(trifluoromethyl)phenyl)quinoline-3-carboxamide | (ESI+) = 333.0846 (M + 1) |
| 50 | 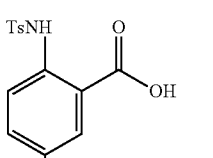 | 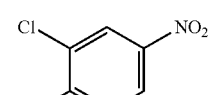 | 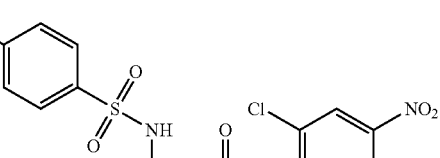 5-chloro-N-(2-chloro-4-nitrophenyl)-2-((4-methylphenyl)sulfonamido)benzamide | (ESI−) = 478 (M − 1) |

-continued

| No | Carboxylic acid | Aniline | Compound | MS (m/z) |
|---|---|---|---|---|
| 51 | MeSO₂NH-(2-COOH, 5-Cl)phenyl | 2-chloro-4-nitroaniline | 5-chloro-N-(2-chloro-4-nitrophenyl)-2-(methylsulfonamido)benzamide | (ESI−) = 402, 404 (M − 1) |
| 52 | MeSO₂NH-(2-COOH, 5-Cl)phenyl | 2-chloro-4-(trifluoromethyl)aniline | 5-chloro-N-(3-chlorophenyl)-2-hydroxybenzamide | (ESI−) = 425, 427 (M − 1) |
| 53 | 4-methoxy-2-hydroxybenzoic acid | 2-chloro-4-nitroaniline | N-(2-chloro-4-nitrophenyl)-2-hydroxy-4-methoxybenzamide | (ESI−) = 321, 323 (M − 1) |
| 54 | 5-chloro-4-methoxy-2-hydroxybenzoic acid | 2-chloro-4-nitroaniline | 5-chloro-N-(2-chloro-4-nitrophenyl)-2-hydroxy-4-methoxybenzamide | (ESI−) = 355, 357 (M − 1) |
| 55 | 5-chloro-4-methoxy-2-hydroxybenzoic acid | 2-chloro-4-fluoroaniline | 5-chloro-N-(2-chloro-4-fluorophenyl)-2-hydroxy-4-methoxybenzamide | (ESI−) = 328, 330 (M − 1) |

| No | Carboxylic acid | Aniline | Compound | MS (m/z) |
|---|---|---|---|---|
| 56 | | | 5-chloro-N-(3-chlorophenyl)-2-hydroxy-4-methoxybenzamide | (ESI−) = 310, 312 (M − 1) |

Example 3. 5-Chloro-2-hydroxy-N-(4-(trifluoromethyl)benzoylbenzamide (57)

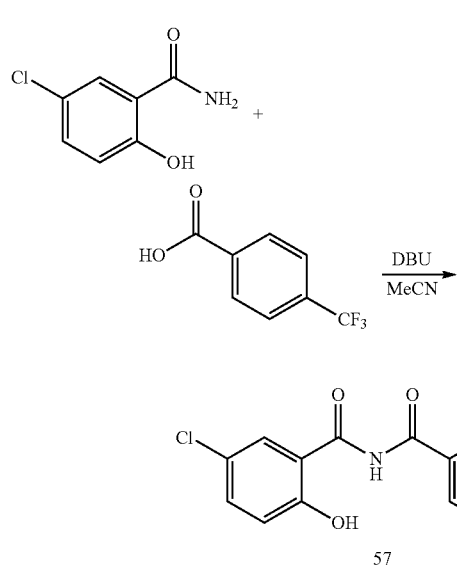

5-Chloro-2-hydroxy-N-(4-(trifluoromethyl)benzoyl)benzamide (57)

To a suspension of 5-chloro-2-hydroxybenzamide (0.579 g, 3.38 mmol) in dry acetonitrile (10 mL) at room temperature was added DBU (1,8-diazabicyclo[5.4.0]undec-7-ene) (1.1 mL, 7.43 mmol). To the resultant solution was added 4-(trifluoromethyl)benzoyl chloride (0.702 g, 3.38 mmol) over 30 sec, and acetonitrile (3 mL) to rinse. The mixture was stirred overnight, water and CH$_2$Cl$_2$ were added, and this mixture extracted with EtOAc and brine to break an emulsion. The organic layer was washed 3 times with 1N HCl, and the aqueous layers combined and back-extracted with EtOAc. The organic layers were combined and washed with brine, dried over Na$_2$SO$_4$ and filtered. The filtrate was concentrated into heptane to induce crystallization. The solids were filtered, rinsed with ether, and dried to yield 0.827 g of the title compound as a white solid. $^1$H NMR (400 MHz, DMSO-d$_6$) δ 11.9 (br s, 1H), 8.05 (d, J=8.15 Hz, 2H), 7.93 (d, J=8.15 Hz, 2H), 7.70 (d, J=2.10 Hz, 1H), 7.43 (dd, J=2.27, 8.37 Hz, 1H), 7.07 (d, J=8.84 Hz, 1H). FTIR (thin film) 3100 br, 1721 st, 1712 st., m/z (ESI−)=342, 344 (M−1).

Example 4. 5-Chloro-N-(2-chloro-4-(trifluoromethyl)phenyl)-2-hydroxybenzenesulfonamide (58)

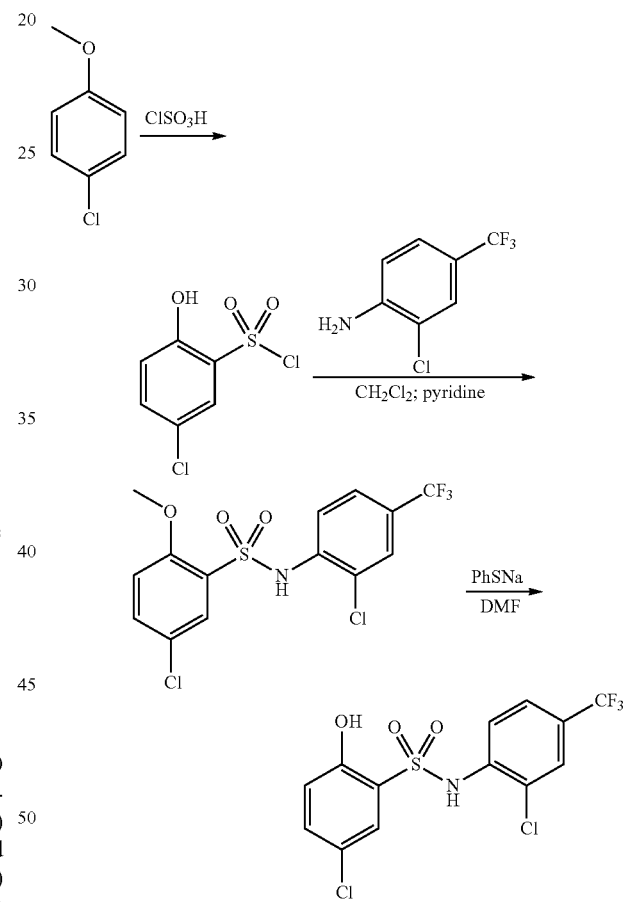

5-Chloro-N-(2-chloro-4-(trifluoromethyl)phenyl)-2-hydroxybenzenesulfonamide (58)

p-Chloroanisole was chlorosulfonylated using the method of Guo (Guo, et al. *Tetrahedron* 1997, 53, 4145) to produce 5-chloro-2-methoxybenzenesulfonyl chloride which was used without purification. To an ice-cold solution of 5-chloro-2-methoxybenzenesulfonyl chloride (0.398 g, 1.8 mmol), CH$_2$Cl$_2$ (5 mL) and pyridine (0.28 g, 3.6 mmol) was added 2-chloro-4-(trifluoromethyl) aniline (0.347 g, 0.18 mmol) over 1 min. After the reaction was complete by HPLC/MS, water was added and the reaction mixture was extracted with $CH_2Cl_2$. The $CH_2Cl_2$ layer was washed three times with dilute acid, one time with brine, dried over $Na_2SO_4$, and filtered through glass wool. The filtrate containing 5-chloro-N-(2-chloro-4-(trifluoromethyl)phenyl)-2-methoxybenzenesulfonamide was concentrated and used directly without further purification. To a dry round-bottom flask containing 5-chloro-N-(2-chloro-4-(trifluoromethyl)phenyl)-2-methoxybenzenesulfonamide in dry DMF (5 mL) was added a solution of freshly prepared 1M sodium benzenethiolate in DMF (3.6 mL). The resultant dark colored mixture was heated in an oil bath at 135-145° C. for 3.5 h, cooled to rt, poured into water (100 mL), and the aqueous mixture extracted 2 times with EtOAc. The EtOAc layers were combined, washed 5 times with water, 1 time with brine, dried with $Na_2SO_4$, decanted, and concentrated onto 5 mL of silica gel. The solids were eluted on a column of 100 mL of silica gel with a gradient of 10-30% EtOAc/Hexane. The material with rf=0.25 (25% EtOAc/Hexane) was combined and concentrated to give 0.22 g of the title compound as a light tan solid. $^1$H NMR (300 MHz, DMSO-$d_6$) δ 11.3 (br s, 1H), 9.9 (br s, 1H), 7.83 (s, 1H), 7.66-7.47 (m, 4H), 6.98 (d, J=8.8, 1H). m/z (ESI−)=384, 386 (M−1). FTIR (thin film) 3339 br, 1615 w, 1323 st, m/z (ESI−)=384, 386 (M−1).

Example 5. 4-Chloro-2-((2-chloro-4-(trifluoromethyl)phenyl)carbamoyl)phenyl acetate (59)

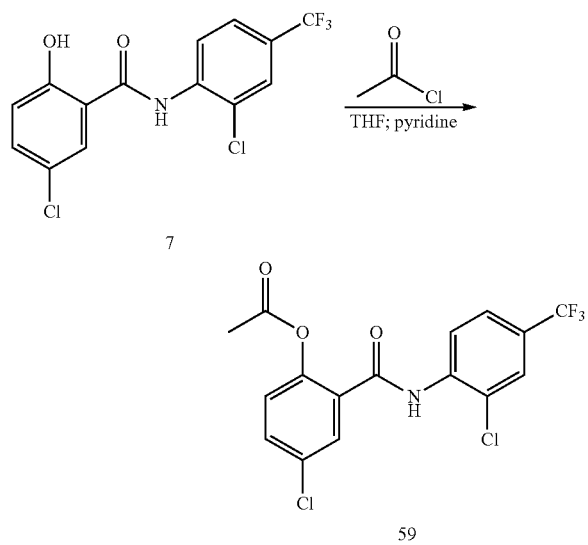

4-Chloro-2-((2-chloro-4-(trifluoromethyl)phenyl)carbamoyl)phenyl acetate (59)

To a round-bottom flask was added 7 (0.140 g, 0.4 mmol), dry THF (5 mL), pyridine (0. 0.036 mL, 0.44 mmol), and acetyl chloride (0.034 g, 0.44 mmol) under an argon atmosphere at room temperature. A white precipitate formed almost immediately. The reaction mixture was stirred at room temperature overnight. The reaction mixture was extracted with $CH_2Cl_2$, washed three times with dilute acid, one time with brine, dried over $Na_2SO_4$, decanted, and concentrated onto 7 mL of silica gel. The solids were eluted from a column of 20 mL of silica gel with 10% EtOAc/Hexane. The fractions containing the desired product were combined and concentrated to give 92 mg of the title compound as a white solid. $^1$H NMR (400 MHz, CDCL3) δ 8.85 (br s, 1H), 8.76 (d, J=8.74 Hz, 1H), 7.98 (d, J=2.59 Hz, 1H), 7.71 (d, J=1.71 Hz, 1H), 7.61 (dd, J=9.2, 1.8 Hz, 1H), 7.54 (dd, J=8.71, 2.61 Hz, 1H), 7.18 (d, J=8.64 Hz, 1H), 2.40 (s, 3H). FTIR (thin film) 3369 sh, 1786 st, 1679 st, m/z (ESI−)=390 (M−1).

The following compounds were made employing analogous synthetic procedures:

| No. | Starting Material | Compound | MS (m/z) |
|---|---|---|---|
| 60 | 30 | 2-((2-(allyloxy)-4-nitrophenyl)carbamoyl)-4-chlorophenyl acetate | (ESI−) = 389 (M − 1), 347 (M − 43) |

Example 6. 4-Chloro-2-((2-chloro-4-nitrophenyl)carbamoyl)phenyl octanoate (61)

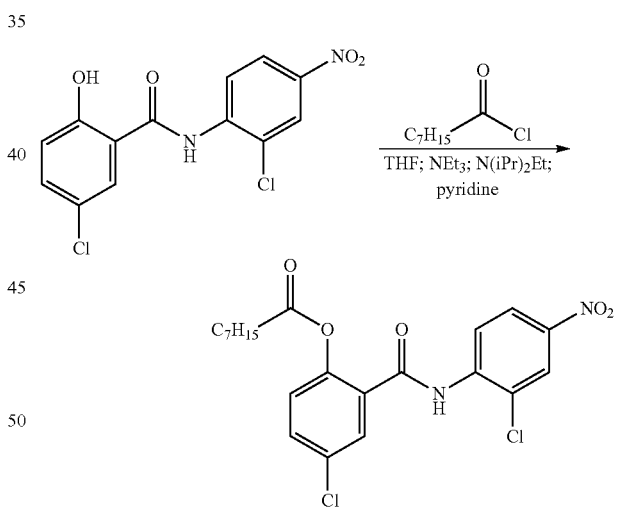

4-Chloro-2-((2-chloro-4-nitrophenyl)carbamoyl)phenyl octanoate (61)

To a dry 500 mL round-bottomed 3-neck flask equipped with thermometer and addition funnel under an argon atmosphere, was added $CH_2Cl_2$ (80 mL) and oxalyl chloride (7 mL, 0.083 mol). To the addition funnel was added $CH_2Cl_2$ (10 mL), DMF (0.5 mL), and octanoic acid (11 mL, 0.069 mol) and this solution added drop-wise over 8 min (rapid gas evolution). After addition was complete the reaction mixture was stirred at rt for 2 hours. Dioxane (20 mL) was added and the flask was fitted with a distillation head. The reaction mixture was concentrated under house vacuum with heating (45-50° C.) to a volume between 10-15 mL. This concentrated mixture was then cooled to room temperature and dry THF (100 mL) was added. In a separate flask was added niclosamide (22.7 g, 0.069 mol), dry THF (200 mL) and to this suspension was added NEt$_3$ (16 mL) and DIEA (10 mL). A majority of the solids dissolved and this mixture was added to the addition funnel, along with 10 mL of dry pyridine. Upon addition of the pyridine a precipitate formed that was suspended in an additional 150 mL of dry THF. This mixture was added to the solution of octanoyl chloride over a total of 15 min. As the niclosamide suspension was added to the acid chloride, the internal temperature began to increase to 28° C. at which point an ice-bath was provided to maintain the temperature between 15-25° C. during the addition. The resultant mixture was stirred over night at room temperature and monitored by HPLC and TLC (30% EtOAC/hexane). The reaction mixture was poured into water and concentrated. The concentrate was diluted with CH$_2$Cl$_2$ and 1N HCl and the mixture filtered. The precipitate was washed with CH$_2$Cl$_2$ and the CH$_2$Cl$_2$ wash combined with the filtrate. The CH$_2$Cl$_2$ layers were combined and were washed three times with 1N HCl, one time with brine, dried over Na$_2$SO$_4$, filtered and concentrated onto 25 mL of silica gel. The solids were eluted from a column of 200 mL of silica gel using a gradient of 7.8:2:0.2 to 7.5:2.5:0.2 hexane/chloroform/EtOAc. The fractions containing the desired compound were combined, heptane was added and the solution concentrated until a large volume of white precipitate was observed. The suspension was allowed to stand overnight, and the precipitate filtered, washed with hexane and dried under vacuum to yield 14.19 g (32.5% over two steps) of the title compound as a white solid. $^1$H NMR (400 MHz, DMSO-d$_6$) δ 10.44 (s, 1H), 8.40 (d, J=2.59 Hz, 1H), 8.27 (dd, J=9.03, 2.59 Hz, 1H), 8.13 (d, J=9.08 Hz, 1H), 7.82 (d, J=2.64 Hz, 1H), 7.69 (dd, J=8.69, 2.64 Hz, 1H), 7.34 (d, J=8.69 Hz, 1H), 2.54 (t, J=7.32 Hz, 2H), 1.48-1.59 (m, 2H), 1.05-1.28 (m, 8H), 0.79 (t, J=7.03 Hz, 3H). $^{13}$C (125 MHz, DMSO-d6) 171.76, 163.67, 147.24, 144.75, 141.22, 132.35, 130.61, 130.42, 129.57, 127.24, 126.02, 125.89, 125.47, 123.53, 33.89, 31.54, 28.87, 28.74, 24.59, 22.50, 14.33. FTIR (thin film) 3362 st, 2950 st, 2935 st, 2855 st, 1770 st, 1685 st, m/z (ESI+)=453, 455 (M+1).

The following compounds were made employing analogous synthetic procedures:

| No. | Starting Material | Compound | MS (m/z) |
|---|---|---|---|
| 62 | niclosamide (B) | 4-chloro-2-((2-chloro-4-nitrophenyl)carbamoyl)phenyl stearate | (ESI+) = 593 (M + 1) FTIR = 1771 cm − 1 |
| 63 | niclosamide (B) | 4-chloro-2-((2-chloro-4-nitrophenyl)carbamoyl)phenyl heptanoate | (ESI−) = 437, 439 (M − 1) |
| 64 | niclosamide (B) | 4-chloro-2-((2-chloro-4-nitrophenyl)carbamoyl)phenyl isobutyrate | (ESI−) = 395, 397 (M − 1) |

-continued

| No. | Starting Material | Compound | MS (m/z) |
|---|---|---|---|
| 65 | niclosamide (B) | tert-butyl (4-chloro-2-((2-chloro-4-nitrophenyl)carbamoyl)phenyl) succinate | (ESI−) = 481, 483 (M − 1) |
| 66 | niclosamide (B) | 4-chloro-2-((2-chloro-4-nitrophenyl)carbamoyl)phenyl 2-propylpentanoate | (ESI+) = 475 (M + Na) |
| 67 | niclosamide (B) | 4-chloro-2-((2-chloro-4-nitrophenyl)carbamoyl)phenyl 6-(2,5-dioxo-2,5-dihydro-1H-pyrrol-1-yl)hexanoate | (ESI−) = 518, 520 (M − 1); IR (FTIR, cm − 1, thin film) = 1769 (m), 1701 (s) |
| 68 | niclosamide (B) | 4-chloro-2-((2-chloro-4-nitrophenyl)carbamoyl)phenyl oleate | (ESI+) = 591 (M + 1), 613 (M + Na) |

| No. | Starting Material | Compound | MS (m/z) |
|---|---|---|---|
| 69 | niclosamide (B) | 4-chloro-2-((2-chloro-4-nitrophenyl)carbamoyl)phenyl (9Z,12Z)-octadeca-9,12-dienoate | (ESI+) = 611 (M + Na) |

Example 7. 4-Chloro-2-((2-chloro-4-(trifluoromethyl)phenyl)carbamoyl)phenyl ethyl carbonate (70)

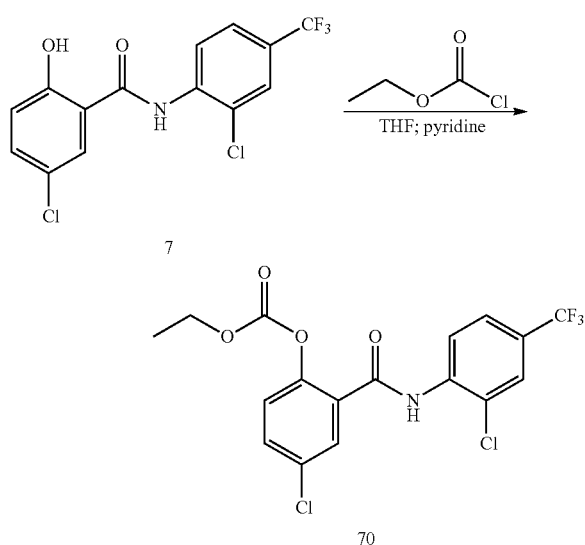

4-Chloro-2-((2-chloro-4-(trifluoromethyl)phenyl)carbamoyl)phenyl ethyl carbonate (70)

To a round-bottom flask was added 7 (0.154 g, 0.44 mmol), dry THF (5 mL), pyridine (0.039 mL, 0.48 mmol), and ethyl chloroformate (0.052 g, 0.48 mmol) under an atmosphere of argon at room temperature. A white precipitate formed almost immediately. The reaction mixture was stirred at room temperature for 44 hours. Water was added and the reaction mixture was extracted with $CH_2Cl_2$. The $CH_2Cl_2$ layer was washed three times with dilute acid, one time with brine, dried over $Na_2SO_4$, decanted, and concentrated onto 7 mL of silica gel. The solids were eluted from a column of 20 mL of silica gel with 10% EtOAc/hexanes. The fractions containing the desired product were combined and concentrated to give 90 mg (48%) of the title compound as a white solid. $^1$H NMR (400 MHz, CDCL3) δ 9.26 (br. s, 1H), 8.76 (d, J=8.69 Hz, 1H), 8.10 (d, J=2.64 Hz, 1H), 7.70 (d, J=1.71 Hz, 1H), 7.52-7.64 (m, 2H), 7.32 (d, J=8.69 Hz, 1H), 4.36 (q, J=7.14 Hz, 2H), 1.37 (t, J=7.08 Hz, 3H). FTIR (thin film) 3359 sh, 1772 st, 1684 st, m/z (ESI+)=422, 424 (M+1).

The following compounds were made employing analogous synthetic procedures:

| No. | Starting Material | Compound | MS (m/z) |
|---|---|---|---|
| 71 | niclosamide (B) | 4-chloro-2-((2-chloro-4-nitrophenyl)carbamoyl)phenyl morpholine-4-carboxylate | (ESI-) = 440, 442 (M - 1) |

-continued

| No. | Starting Material | Compound | MS (m/z) |
|---|---|---|---|
| 72 | niclosamide (B) | 4-chloro-2-((2-chloro-4-nitrophenyl)carbamoyl)phenyl octyl carbonate | (ESI−) = 481, 483 (M − 1) |

Example 8. 6-Chloro-3-(2-chloro-4-(trifluoromethyl)phenyl)-2H-benzo[e][1,3]oxazine-2,4(3H)-dione (73)

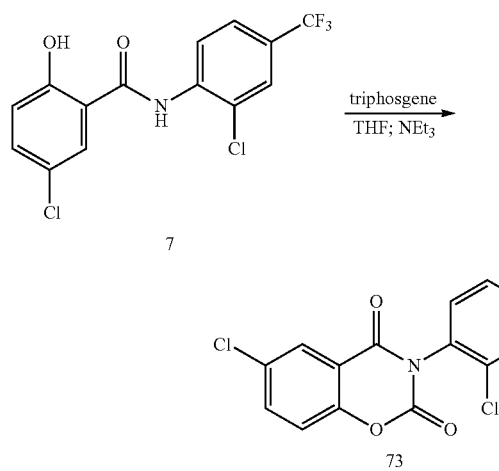

6-Chloro-3-(2-chloro-4-(trifluoromethyl)phenyl)-2H-benzo[e][1,3]oxazine-2,4(3H)-dione (73)

To a round-bottom flask equipped with a reflux condenser was added 7 (0.82 g, 2.34 mmol), dry THF (15 mL), and NEt₃ (0.81 mL, 5.86 mmol) under an atmosphere of argon. Triphosgene (0.76 g, 2.6 mmol) was dissolved in dry THF and this solution added to the reaction flask over 1 min. The flask warms and a white precipitate formed. The mixture was stirred at room temperature for 1.5 hours, then placed into an oil-bath and heated to reflux for 2.5 hours, and cooled to room temperature and stirred overnight. The mixture was extracted with $CH_2Cl_2$, washed three times with dilute acid, one time with brine, dried over $Na_2SO_4$, decanted, and concentrated onto 10 mL of silica gel. The solids were eluted from a column of 100 mL of silica gel with 1:1 hexane/chloroform to give the title compound as a white solid. ¹H NMR (500 MHz, DMSO-d₆) δ 8.22 (d, J=1.8 Hz, 1H), 8.06 (d, J=2.5 Hz, 1H), 8.03-7.98 (m, 2H), 7.93 (d, J=7.95 Hz, 1H), 7.69 (d, J=8.8 Hz, 1H). ¹³C (75 MHz, DMSO-d6) δ=159.25, 151.76, 146.48, 137.34, 136.43, 133.43, 132.51, 130.46, 127.57, 127.03, 126.1, 119.61, 115.92. DK4-86-3 IR (thin film) 1766, 1706 cm⁻¹. HRMS m/z (ESI+)=375.9747 (M+1), calculated C15H7Cl2F3NO3=375.975 error=0.8 ppm.

The following compounds were made employing analogous synthetic procedures:

| No. | Starting Material | Compound | MS (m/z)/¹H NMR |
|---|---|---|---|
| 74 | 8 | 6-chloro-3-(4-(trifluoromethyl)phenyl)-2H-benzo[e][1,3]oxazine-2,4(3H)-dione | (ESI+) = 341.0138 (M + 1) |
| 75 | niclosamide (B) | 6-chloro-3-(2-chloro-4-nitrophenyl)-2H-benzo[e][1,3]oxazine-2,4(3H)-dione | ¹H NMR (400 MHz, DMSO-d₆) δ 8.55 (d, J = 2.53 Hz, 1H), 8.39 (dd, J = 8.52, 2.59 Hz, 1H), 8.4-7.92 (m, 3H), 7.65 (d, J = 8.96 Hz, 1H); (ESI−) = 324.9 (M − CO + 1) |

| No. | Starting Material | Compound | MS (m/z)/$^1$H NMR |
|---|---|---|---|
| 76 | 10 | 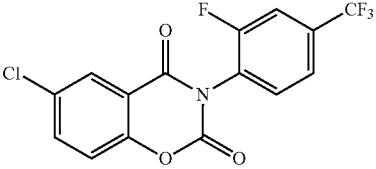 [SMILES: O=c1oc2ccc(Cl)cc2c(=O)n1-c1ccc(C(F)(F)F)cc1F]<br>6-chloro-3-(2-fluoro-4-(trifluoromethyl)phenyl)-2H-benzo[e][1,3]oxazine-2,4(3H)-dione | $^1$H NMR (400 MHz, DMSO-d$_6$) δ 8.1 (m, 3H), 7.87 (m, 2H), 7.64 (d, J = 9 Hz, 1H). |

Example 9. 4-Chloro-2-((2-chloro-4-nitrophenyl)(heptanoyl)carbamoyl)phenyl heptanoate (77) or 5-Chloro-N-(2-chloro-4-nitrophenyl)-2-(heptanoyloxy)benzimidic heptanoic anhydride (78)

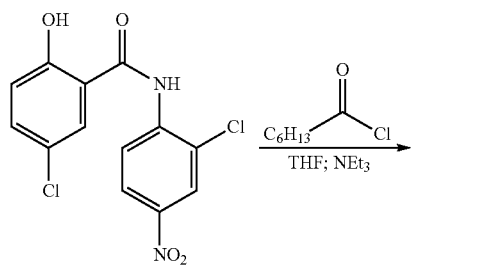

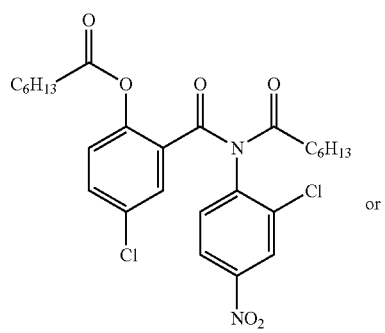

77

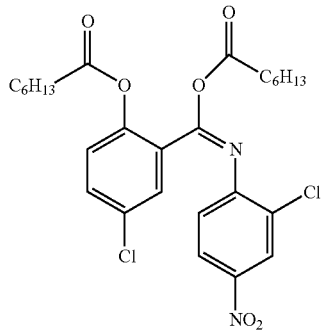

78

4-Chloro-2-((2-chloro-4-nitrophenyl)(heptanoyl)carbamoyl)phenyl heptanoate (77) or 5-Chloro-N-(2-chloro-4-nitrophenyl)-2-(heptanoyloxy)benzimidic heptanoic anhydride (78)

Figure 2:
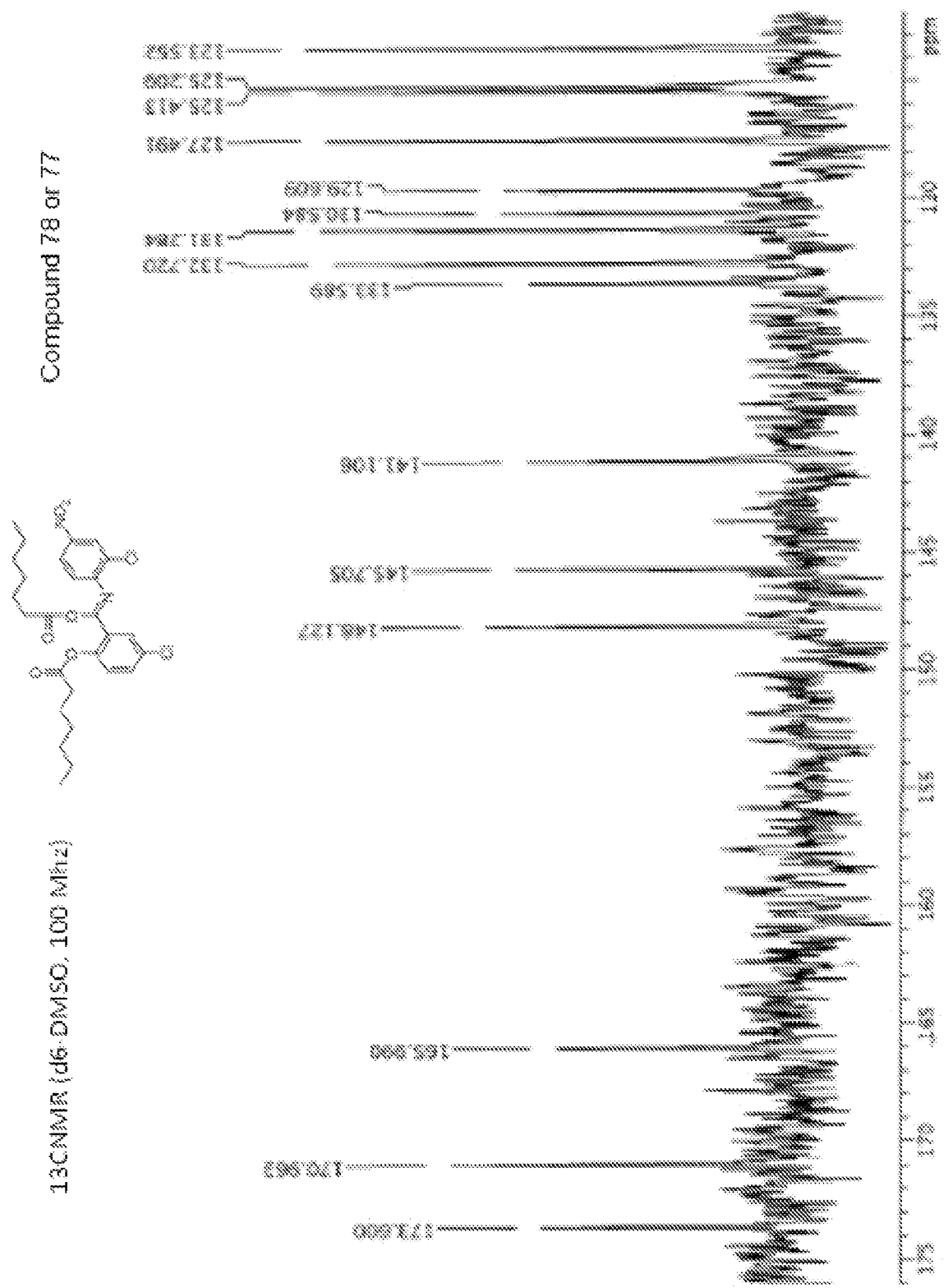
FIG. 2 is a $^{13}$C-NMR spectrum of an exemplary compound.
Figure 3:
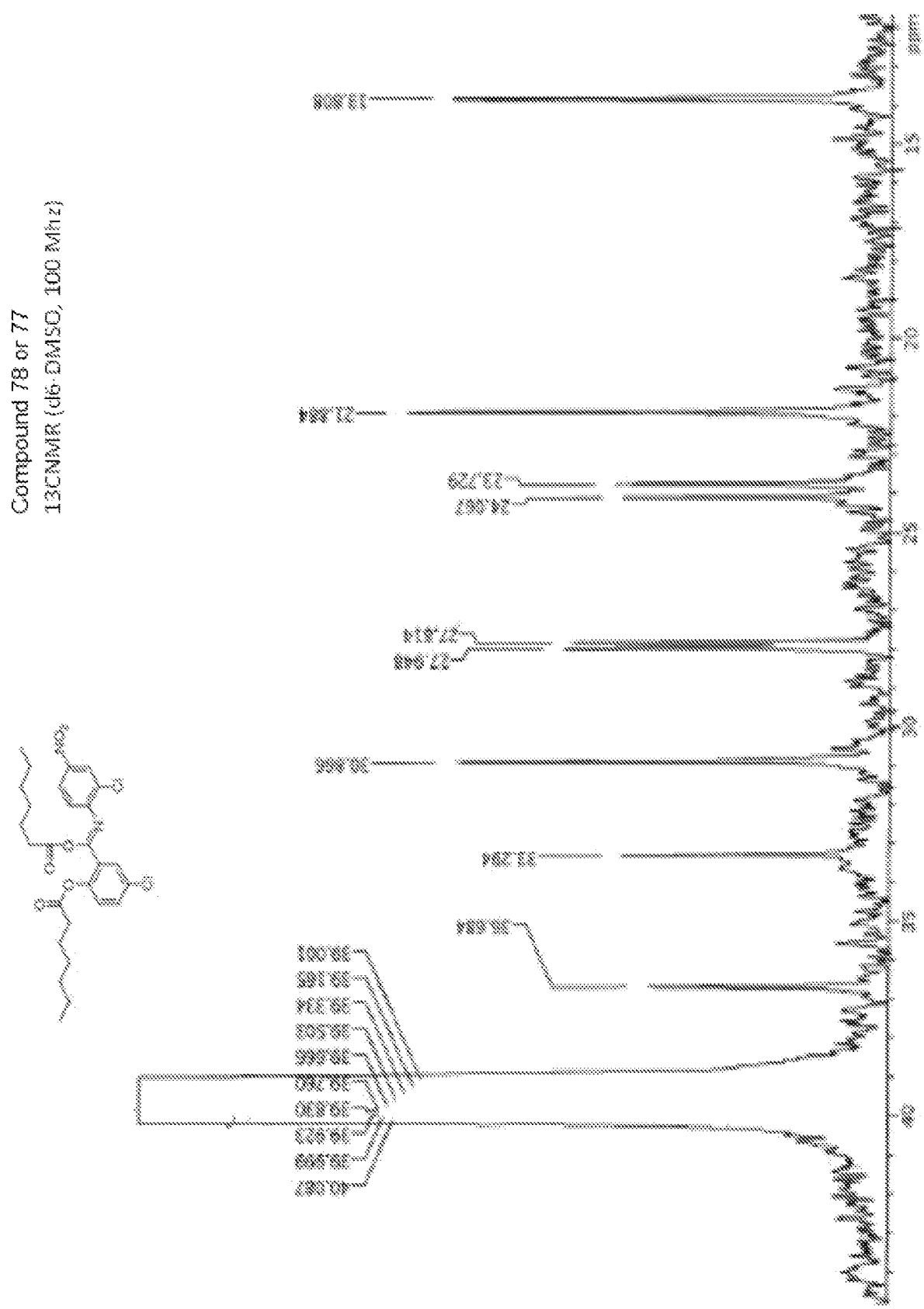
FIG. 3 is a $^{13}$C-NMR spectrum of an exemplary compound.

To a dry round-bottomed flask under an argon atmosphere was added dry THF (5 mL) and heptanoyl chloride (0.56 g, 3.85 mmol). In a separate flask was added niclosamide (0.57 g, 1.75 mmol) and dry THF (5 mL). To this suspension was added NEt$_3$ (0.3 mL) to produce a red colored solution. To this solution was added pyridine (0.73 mL), and the resultant mixture was added to the flask containing the heptanoyl chloride over 5 min at room temperature. The resultant mixture was stirred overnight and could be monitored by HPLC and TLC (EtOAC/hexane). The reaction mixture was poured into a mixture of CH$_2$Cl$_2$ and water and the organic layers were separated and washed 3-4 times with pH 3 buffer until the aqueous layer remained near pH3. The organic layer was then dried over Na$_2$SO$_4$, filtered and concentrated to a dark oil. The oil was purified in portions by reverse phase HPLC on a C18 column (Ascentis, 5, 25 cm×21.2 mm) using a flow rate of 20 mL/min and a linear gradient over 30 min of 40-98% CH$_3$CN/H$_2$O containing 0.2% formic acid. The fractions containing the desired material were concentrated and extracted with CH$_2$Cl$_2$ and freshly prepared saturated sodium bicarbonate. The organic layer was dried over Na$_2$SO$_4$, filtered, and concentrated to an oil that solidified slowly at −20° C. HRMS (ESI+)=573.1531 (M+Na). FTIR (thin film)=1767.86, 1717.76 cm$^{-1}$. See FIG. 1-3 for NMR data.

Characterization data of the isolated product suggests that the structure is consistent with compound 78. Studies remain ongoing to determine, without ambiguity, the structural identity of the product of the reaction described above.

Using an analogous procedure with octyl chloroformate, compound 79 (or 80) was prepared. Characterization data of the isolated product suggests that the structure is consistent with compound 79. See FIG. 4 for NMR data. Studies remain ongoing to determine, without ambiguity, the structural identity of the product formed.

| No. | Compound | MS (m/z) |
|---|---|---|
| 79 | 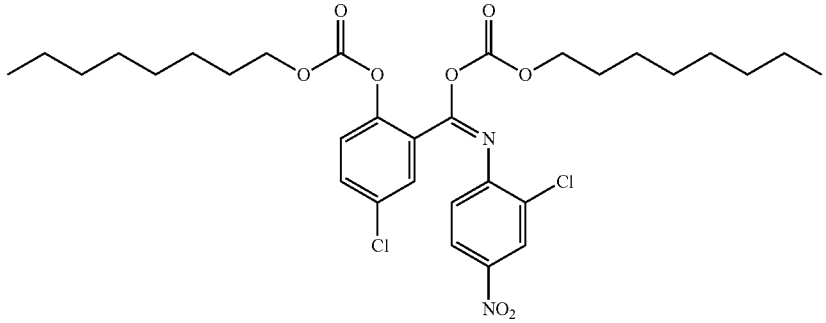 [SMILES: CCCCCCCCOC(=O)O/C(=N/c1ccc([N+](=O)[O-])cc1Cl)c1cc(Cl)ccc1OC(=O)OCCCCCCCC]<br>5-chloro-N-(2-chloro-4-nitrophenyl)-2-(((octyloxy)carbonyl)oxy)benzimidic (octyl carbonic) anhydride | ES(−) = 481<br>(M − $C_9H_{17}O_2$) |
| 80 | 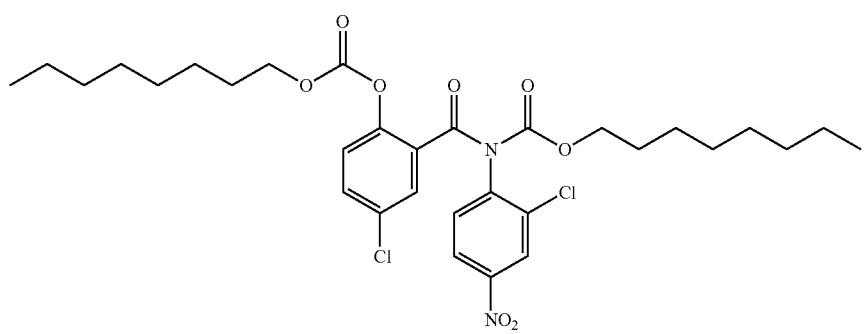 [SMILES: CCCCCCCCOC(=O)Oc1ccc(Cl)cc1C(=O)N(C(=O)OCCCCCCCC)c1ccc([N+](=O)[O-])cc1Cl]<br>octyl (5-chloro-2-(((octyloxy)carbonyl)oxy)benzoyl)(2-chloro-4-nitrophenyl)carbamate | ES(−) = 481<br>(M − $C_9H_{17}O_2$) |

Example 10. Commercial Compounds

The following known compounds were purchased from commercial sources:

| compound | Structure and name |
|---|---|
| A | 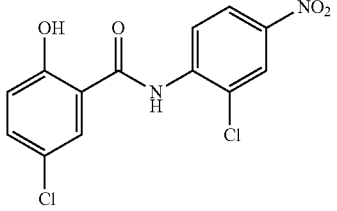 [SMILES: O=C(Nc1ccc([N+](=O)[O-])cc1Cl)c1cc(Cl)ccc1O]<br>5-chloro-N-(2-chloro-4-nitrophenyl)-2-hydroxybenzamide (niclosamide) |
| B | 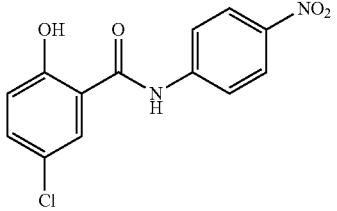 [SMILES: O=C(Nc1ccc([N+](=O)[O-])cc1)c1cc(Cl)ccc1O]<br>5-chloro-2-hydroxy-N-(4-nitrophenyl)benzamide |
| C | 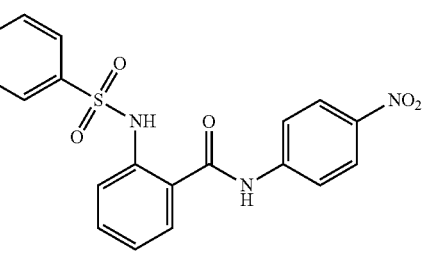<br>2-((4-methylphenyl)sulfonamido)-N-(4-nitrophenyl)benzamide |
| D | 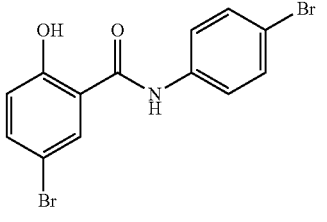 [SMILES: O=C(Nc1ccc(Br)cc1)c1cc(Br)ccc1O]<br>5-bromo-N-(4-bromophenyl)-2-hydroxybenzamide |

Example 11. In Vitro Biological Activity

A. Frizzled Internalization Assay (Fzd1-GFP)

The Fzd1-GFP assay was performed following a procedure similar to previously published work (Chen, M. Y.; Wang, J. B.; Lu, J. Y.; Bond, M. C.; Ren, X. R.; Lyerly, H. K.; Barak, L. S.; Chen, W. *Biochemistry* 2009, 48, 10267). Cells stably expressing Frizzled1-GFP plated in confocal dishes were treated, after 24 hours, with 12.5 µM of test compound or DMSO for 6 hours at 37° C. followed by fixation with 4% paraformaldehyde. The cells were then examined by microscopy using a LSM 510-Meta confocal microscope (Carl Zeiss, Thornwood, N.Y., USA) equipped with 40× and 100× apo chromat objectives. YFP was excited using a 488-nm argon laser line. Images were processed using the LSM software Image Browser (CarlZeiss, Thornwood, N.Y., USA). Plates were read twice in blinded fashion using a 0-5 point scale. $^a$Punctate similar to control=0, trace amount of punctate greater than control=1, moderate=3, strong=5.

B. TOPFlash Reporter Assay

Wnt-3A conditioned medium was prepared using L WNT-3A cells (ATCC R CRL-2647™) purchased from ATCC. Conditioned medium was obtained following published protocols (http://www.atcc.org/Products/All/CRL-2647.aspx# culturemethod) (Chen, M. Y.; Wang, J. B.; Lu, J. Y.; Bond, M. C.; Ren, X. R.; Lyerly, H. K.; Barak, L. S.; Chen, W. *Biochemistry* 2009, 48, 10267). HEK293 cells were stably transfected with p8xTOPFlash, *Renilla* luciferase plasmid pRL-TK (Promega), and pLKO.1 as previously published (Chen, M. Y.; Wang, J. B.; Lu, J. Y.; Bond, M. C.; Ren, X. R.; Lyerly, H. K.; Barak, L. S.; Chen, W. *Biochemistry* 2009, 48, 10267). Stably transfected cells were seeded in 100 µl of cell growth medium/well in 96-well plates at 100% confluency. Fifty microliters of Wnt-3A conditioned medium containing the chemical compounds to be tested or DMSO was added to each well. After an 8 hour treatment, the cells were washed once with PBS and lysed with 55 µl of Passive Lysis Buffer supplied in the Dual-Luciferase Reporter Assay kit (Promega, Madison, Wis.). Twenty-five microliters of cell lysate was used for measuring luciferase activity in a 96-well plate reader (FluoStar Optima, BMG Labtech, Chicago, Ill.). Data were fit using GraphPad Prism (mean±SEM, n>=2).

C. Western Blot Analysis

Western blots were performed following a procedure similar to previously published work (Osada, T.; Chen, M. Y.; Yang, X. Y.; Spasojevic, I.; Vandeusen, J. B.; Hsu, D.; Clary, B. M.; Clay, T. M.; Chen, W.; Morse, M. A.; Lyerly, H. K. *Cancer Research* 2011, 71, 4172). HCT-116 cells were grown to about 80% confluency in poly-D-lysine coated six-well plates 48 hours before treatment and followed by 2.0 µM compounds or DMSO incubation for 18 hours in growth medium. After treatment, the cytosolic fraction was isolated as described (Osada, T.; Chen, M. Y.; Yang, X. Y.; Spasojevic, I.; Vandeusen, J. B.; Hsu, D.; Clary, B. M.; Clay, T. M.; Chen, W.; Morse, M. A.; Lyerly, H. K. *Cancer Research* 2011, 71, 4172). Immunoblots using antibodies to 1-catenin (E-5, Santa Cruz Biotechnology catalog number sc-7963) was used to detect β-catenin protein levels in the cytosol, and immunoblots using antibodies to β-actin (C-4, Santa Cruz Biotechnology, catalog number SC-47778) was used for loading controls.

D. Cell Proliferation Assay

The colon cancer cell line HCT116 was used in the cell proliferation assay. The cells were plated in 100 µl of growing medium/well in 96-well plates at 5,000 cells per well and treated with compounds from 0.04 to 10 µM for 72 hours, after which point the cells were analyzed by colorimetric MTS assay (Promega, Madison, Wis., USA). Data were fit using GraphPad Prism (mean±SEM, n 3).

E. Results and Discussion of In Vitro Biological Activity Data

The results of the Fzd1-GFP and Topflash Reporter assays are shown in Table 1. The data in Table 1 demonstrates that the disclosed compounds are inhibitors of the Wnt/Frizzled signaling pathway. Data is from a single experiment unless otherwise noted. Data that is an average of two experiments is noted as "n=2" while data that is an average of three or more experiments is presented as the average plus or minus the standard error of the mean.

The Fzd1-GFP and the Wnt-stimulated TOPFlash assays were employed to interrogate the SAR of the disclosed compounds. Whereas these studies did not identify molecules more potent than niclosamide, they did identify compounds with similar potency and better overall handling and solubility properties than niclosamide in solvents used in synthesis and purification. In particular, compounds in which the nitro substituent was replaced with a trifluoromethyl group or a chlorine group were similar in potency to niclosamide in both the FZD1-GFP internalization and the Wnt3A-stimulated β-catenin TOPFlash transcription assays (compounds 7, 8 and 14, Table 1).

TABLE 1

| Compound | Fzd1-GFP internalization @12.5 µM$^a$ | Inhibition Wnt/β-catenin transcription TopFlash IC50 (µM) | clogP | pKa (NH) | pKa (OH) |
|---|---|---|---|---|---|
| A | 5 | 0.34 ± 0.08 | 3.1 | 11.2 | — |
| B | — | >12 | 2.2 | 12.1 | 8.3 |
| C | — | 47% inhibition @ 1 µM | — | — | — |
| D | — | 60% inhibition @ 2 µM | — | — | — |
| 1 | 0 | 11.81 | 3.3 | 13.2 | — |
| 2 | 5 | 0.99 ± 0.32 | 2.7 | 12.1 | — |
| 3 | 0 | 6.42 ± 0.51 | 3.0 | 12.5 | — |
| 4 | 0 | >12 | 1.9 | 12.7 | — |
| 5 | 0 | 7.66 | 2.6 | 11.4 | — |
| 6 | 0 | 15.04 | 4.2 | 12.5 | — |
| 7 | 5 | 0.56 ± 0.21 | 4.8 | 11.9 | — |
| 8 | 5 | 0.29 ± 0.06 | 4.5 | 12.4 | — |
| 9 | 5 | 0.89 ± 0.32 | 4.7 | 12.5 | — |
| 10 | 5 | 0.55 ± 0.11 | 4.5 | 11.8 | — |
| 11 | 0 | 1.30 ± 0.18 | 4.0 | 12.8 | — |
| 12 | 5 | 1.65 ± 0.12 | 4.0 | 12.6 | — |
| 13 | 1 | 3.05 ± 0.87 | 3.9 | 12.3 | — |
| 14 | 5 | 0.42 ± 0.10 | 4.5 | 11.9 | — |
| 15 | 5 | 0.75 ± 0.13 | 4.4 | 11.7 | — |
| 16 | 5 | 0.70 ± 0.13 | 4.5 | 12.0 | — |
| 17 | 5 | 0.73 ± 0.13 | 4.5 | 12.2 | — |
| 18 | 0 | >12 | 4.3 | 11.4 | — |
| 19 | 0 | 3.84 ± 0.29 | 3.9 | 13.1 | — |
| 20 | 2 | 4.02 ± 0.79 | 4.0 | 12.6 | — |
| 21 | — | >12 | 3.9 | 12.1 | — |
| 22 | 3 | 1.41 ± 0.21 | 4.4 | 12.2 | — |
| 23 | 5 | 1.21 ± 0.17 | 4.4 | 12.5 | — |
| 24 | 0 | >12 | 4.5 | — | 8.4 |
| 25 | 0 | 15.1 ± 1.4 | 4.6 | 12.0 | 8.4 |
| 26 | — | 80% inhibition @ 3 µM | — | — | — |
| 27 | — | 75% inhibition @ 2 µM | — | — | — |
| 28 | — | 82% inhibition @ 1 µM | — | — | — |
| 29 | — | >12 | — | — | — |
| 30 | — | 98% inhibition @ 10 µM | — | — | — |
| 31 | — | 55% inhibition @ 2 µM | — | — | — |

TABLE 1-continued

| Compound | Fzd1-GFP internalization @12.5 μM[a] | Inhibition Wnt/β-catenin transcription TopFlash IC50 (μM) | clogP | pKa (NH) | pKa (OH) |
|---|---|---|---|---|---|
| 32 | — | 90% inhibition @ 10 μM | — | — | — |
| 33 | — | 45% inhibition @ 2 μM | — | — | — |
| 34 | — | 40% inhibition @ 10 μM | — | — | — |
| 35 | — | 40% inhibition @ 10 μM | — | — | — |
| 36 | — | 90% inhibition @ 2 μM | — | — | — |
| 37 | — | 40% inhibition @ 2 μM | — | — | — |
| 38 | — | 90% inhibition @ 2 μM | — | — | — |
| 39 | — | 80% inhibition @ 2 μM | — | — | — |
| 40 | — | 33 | — | — | — |
| 41 | — | 90% inhibition @ 1 μM | — | — | — |
| 42 | — | 90% inhibition @ 2 μM | — | — | — |
| 43 | — | 50% inhibition @ 5 μM | — | — | — |
| 44 | — | 80% inhibition @ 5 μM | — | — | — |
| 45 | — | 60% inhibition @ 5 μM | — | — | — |
| 46 | — | No inhibit. up to 12 μM | — | — | — |
| 47 | — | stimulates | — | — | — |
| 48 | — | 93% inhibition @ 10 μM | — | — | — |
| 49 | — | Stimulates up to 12 μM | — | — | — |
| 50 | — | 80% inhibition @ 5 μM | — | — | — |
| 51 | — | 70% inhibition @ 10 μM | — | — | — |
| 52 | — | 70% inhibition @ 5 μM | — | — | — |
| 53 | — | 70% inhibition @ 2 μM | — | — | — |
| 54 | — | 70% inhibition @ 1 μM | — | — | — |
| 55 | — | 70% inhibition @ 10 μM | — | — | — |
| 56 | — | No inhibition up to 10 μM | — | — | — |
| 57 | 0 | >12 | 4.2 | 11.9 | 7.4 |
| 58 | 1 | 2.57 ± 0.27 | 3.8 | 6.2 | 6.6 |
| 59 | 5 | 0.32 ± 0.03 | 4.2 | 9.6 | — |
| 60 | — | 80% inhibition @ 2 μM | — | — | — |
| 61 | 5 | 0.23 ± 0.06 | 4.3 | 9.4 | — |
| 62 | — | 70% inhibition @ 10 μM | — | — | — |
| 63 | — | 0.5 | — | — | — |
| 64 | — | 70% inhibition @ 0.5 μM | — | — | — |
| 65 | — | 60% inhibition @ 0.5 μM | — | — | — |
| 66 | — | 30% inhibition @ 0.5 μM | — | — | — |
| 67 | — | 75% inhibition @ 0.5 μM | — | — | — |
| 68 | — | 60% inhibition @ 2 μM | — | — | — |
| 69 | — | 85% inhibition @ 2 μM | — | — | — |
| 70 | 5 | 0.34 ± 0.12 | 4.8 | 10.5 | — |
| 71 | — | 60% inhibition @ 20 μM | — | — | — |
| 72 | — | 0.5 | — | — | — |
| 73 | 5 | 0.33 ± 0.10 | 4.3 | — | — |
| 74 | 5 | 0.32 ± 0.03 | 3.9 | — | — |
| 75 | — | 0.37 ± 0.13 | 2.6 | — | — |
| 76 | — | 90% @ 1 μM | — | — | — |
| 77 | — | 1.6 | — | — | — |
| 78 | — | — | — | — | — |
| 79 | — | 0.8 | — | — | — |
| 80 | — | — | — | — | — |

ClogP and pKa values were calculated in Maestro 9.3 (Schrodinger, Inc.) using Qikprops and Epik. Calculated pKa values in water are reported. Calculated value of the pKa of the —OH group is 6.8 in each example listed. The calculated pKa of the NH is the salicylamide NH without ionization of the —OH group. The estimated error of the pKa calculation for the OH group is ±1 log unit, and ±2 for the NH group.

To further characterize the Wnt inhibitory and the cancer cell anti-proliferation activity, selected active compounds were evaluated in HCT-116 colorectal cancer cell culture in comparison with inactive compounds (compounds 18 and 58). Inhibition of Wnt signaling was determined by analyzing the reduction of cytosolic β-catenin by Western blot (FIG. 1, 2). Upon treating cells with 2.0 μM of compound for 18 hours in culture, β-catenin levels were significantly decreased only by the compounds that showed activity in the FZD1-GFP and Wnt-3A stimulated TOPFlash assay. The results are reported in Table 2.

TABLE 2

| compound | Remaining cytosolic β-catenin (μM) | compound | Remaining cytosolic β-catenin (μM) |
|---|---|---|---|
| A | 8% | A | 10% |
| 7 | 6% | 61 | 8% |
| 8 | 7% | 70 | 8% |
| 14 | 7% | 73 | 9% |
| 18 | 100% | 24 | 96% |

Anti-proliferation activity was also measured by MTS assay. In this assay, the inactive derivatives, compounds 18 and 58, had no effect up to 10 μM. In contrast, the compounds that were active in the FZD1-GFP internalization assay, the Wnt3A-stimulated TOPFlash assay and the β-catenin Western blot assay were also active in the MTS assay. The results are reported in Table 3.

TABLE 3

| compound | IC$_{50}$ (μM) | compound | IC$_{50}$ (μM) |
|---|---|---|---|
| A | 0.45 ± 0.05 | A | 0.45 ± 0.05 |
| 7 | 0.54 ± 0.08 | 61 | 0.61 ± 0.11 |
| 8 | 0.67 ± 0.09 | 70 | 0.51 ± 0.06 |
| 14 | 1.18 ± 0.14 | 73 | 0.55 ± 0.07 |
| 18 | >10 | 24 | >10 |

Example 12. In Vivo Studies

A. Pharmacokinetic Studies

For niclosamide dosed IV, niclosamide was dissolved in a solvent of 67% polyethylene glycol 400 and 33% N,N-dimethylacetamide at a concentration of 3.27 mg/mL and tail vein injected at a dose of 2.6 mg/kg of body weight. Blood samples were obtained at predose and at 0.08, 0.17, 0.33, 0.67, 1.5, 4, 8, 12 hours after drug administration. For oral dosing of compound 74, compound 74 was dissolved in a solvent of 90% polyethylene glycol 300 and 10% 1-methyl-2-pyrrolidinone at a concentration of 20 mg/mL and gavaged at a dose of 200 mg/kg of body weight. Blood samples were obtained at predose and at 0.25, 0.5, 1, 2, 4, 8 hours after drug administration. For oral dosing of compound 61, compound 61 was dissolved in corn oil at a concentration of 20 mg/mL and dosed at 200 mg/kg of body weight. Blood samples were obtained at predose and at 0.25, 0.5, 0.75, 1, 1.5, 4, 8, 12, 24, 48, and 72 hours after drug administration. All the solvent reagents were purchased from Sigma-Aldrich (St. Louis, Mo., USA). CD1 mice were used in the pharmacokinetic studies. Quantification of niclosamide in mouse plasma was done by LC/MS-MS using methods similar to those previously published (Osada, T.; Chen, M. Y.; Yang, X. Y.; Spasojevic, I.; Vandeusen, J. B.; Hsu, D.; Clary, B. M.; Clay, T. M.; Chen, W.; Morse, M. A.; Lyerly, H. K. *Cancer Research* 2011, 71, 4172.).

B. Toxicity Studies

NOD/SCID mice received oral administration of vehicle (corn oil) or compound 61 (200 mg/kg in corn oil) 6 days per week for 3 weeks. The animals were observed throughout the period for any side effects. The body weights were measured the same day of the first dosing (week 0) and the day after the last dosing (week 3).

C. Results and Discussion of In Vivo Studies

Initial experiments in mice revealed that compounds 7 and 74 possessed poor pharmacokinetic properties after oral administration, similar to that of niclosamide.

Having replaced the nitro group (site of metabolism), and blocked the phenolic site of ionization and glucuronidation, it was surmised that the parameter now limiting oral exposure may be poor solubility in aqueous media. Given the compounds are somewhat hydrophobic with c log P values of 4-5, an oil-based vehicle was employed. Compound 61 was formulated in corn oil and dosed orally to mice at 200 mg/kg, resulting in significantly increased plasma exposure of niclosamide (FIG. 3) when compared to published studies of 200 mg/kg Niclosamide dosed orally (Osada, T.; Chen, M. Y.; Yang, X. Y.; Spasojevic, I.; Vandeusen, J. B.; Hsu, D.; Clary, B. M.; Clay, T. M.; Chen, W.; Morse, M. A.; Lyerly, H. K. *Cancer Research* 2011, 71, 4172.). Cmax, AUC and the duration of exposure of niclosamide obtained by dosing compound 61 were all increased by a surprising amount, even though on a molar basis, the amount of compound 61 dosed was approximately ⅓ less than the amount of niclosamide dosed. In fact, the plasma levels of niclosamide obtained by dosing compound 61 at 200 mg/kg were above the $IC_{50}$ of inhibition of Wnt signaling in the TOPFlash assay for nearly 24 hours, whereas the reported plasma levels of niclosamide dosed as a solution at 200 mg/kg were only above the $IC_{50}$ of Wnt inhibition in the TOPFlash assay for less than 1 hour (Osada, T.; Chen, M. Y.; Yang, X. Y.; Spasojevic, I.; Vandeusen, J. B.; Hsu, D.; Clary, B. M.; Clay, T. M.; Chen, W.; Morse, M. A.; Lyerly, H. K. *Cancer Research* 2011, 71, 4172.). The results of the pharmacokinetic experiment for compound 61 are summarized in Table 4.

TABLE 4

| PK parameter | result |
| --- | --- |
| Tmax | 0.75 hr |
| Cmax | 6.1 ug/mL |
| Tlast | 72 hr |
| Clast | 0.049 ug/mL |
| AUClast | 22.4 ug h/mL |
| $t_{1/2}$ (45 min-4 h) | 0.69 hr |
| $t_{1/2}$ (24-48 h) | 12.2 hr |

Figure 4:
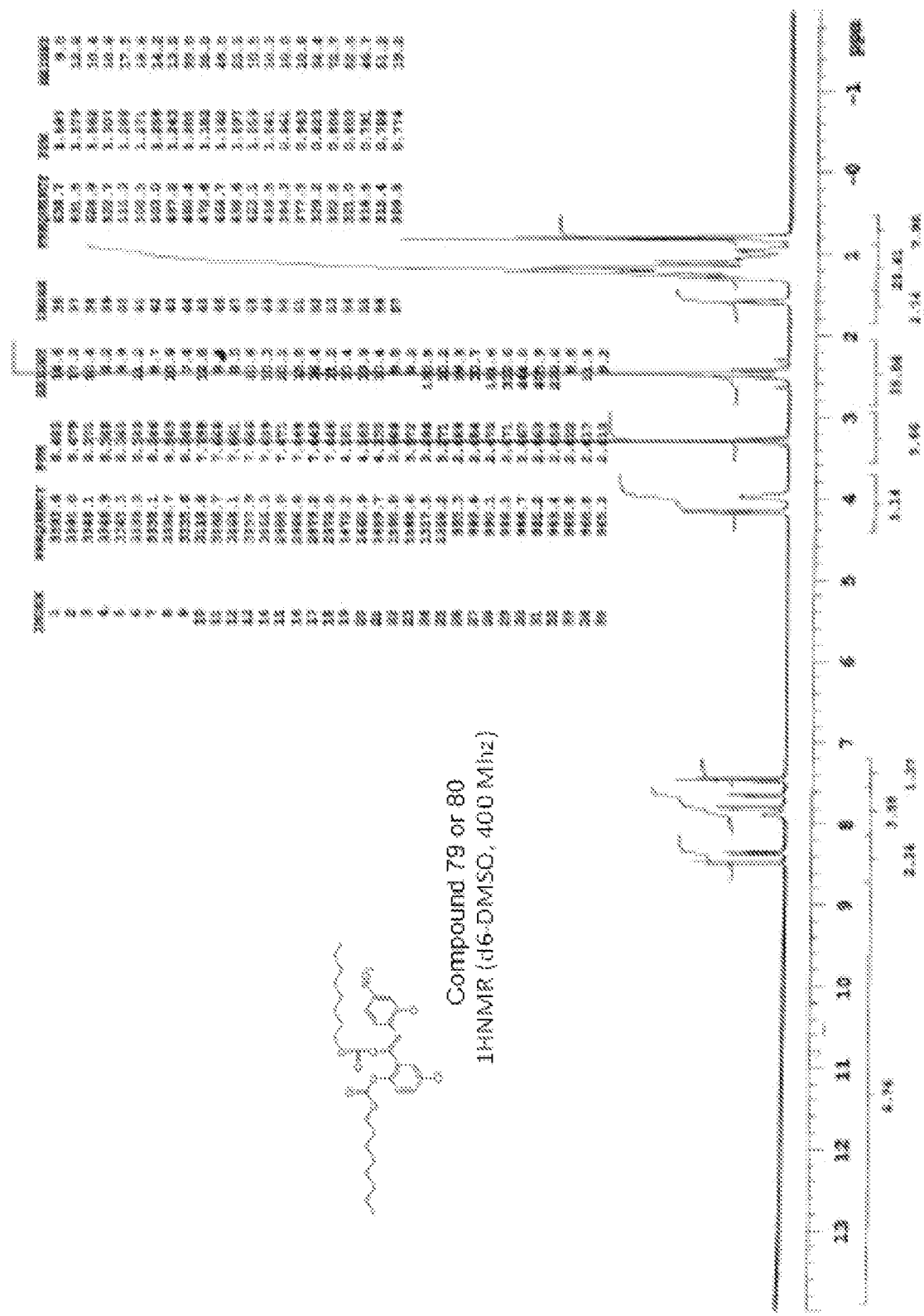
FIG. 4 is a $^1$H-NMR spectrum of an exemplary compound.
Figure 5:
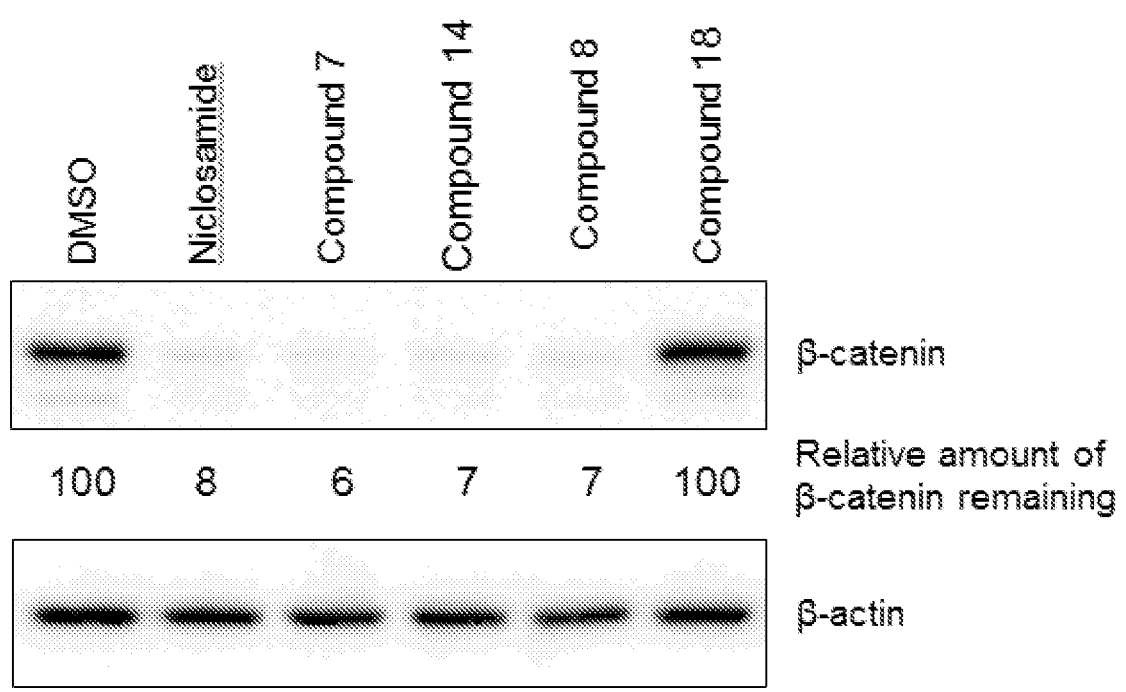
FIG. 5 is a Western blot analysis showing reduction of cytosolic β-catenin levels upon treatment with exemplary compounds.
Figure 6:
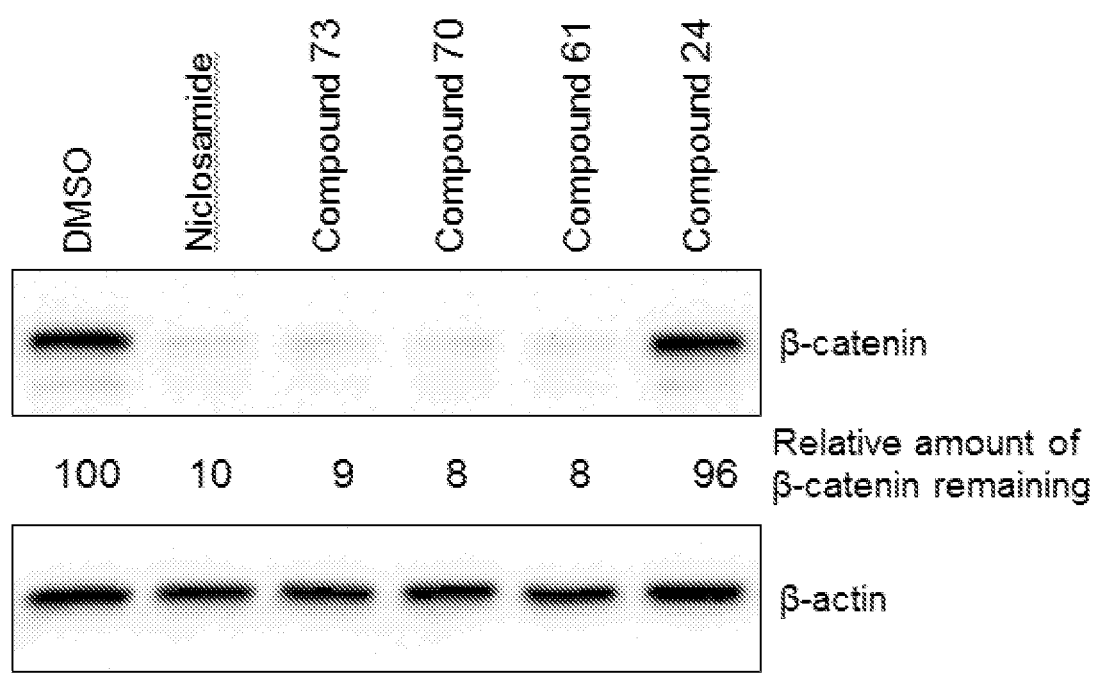
FIG. 6 is a Western blot analysis showing reduction of cytosolic β-catenin levels upon treatment with exemplary compounds.
Figure 7:
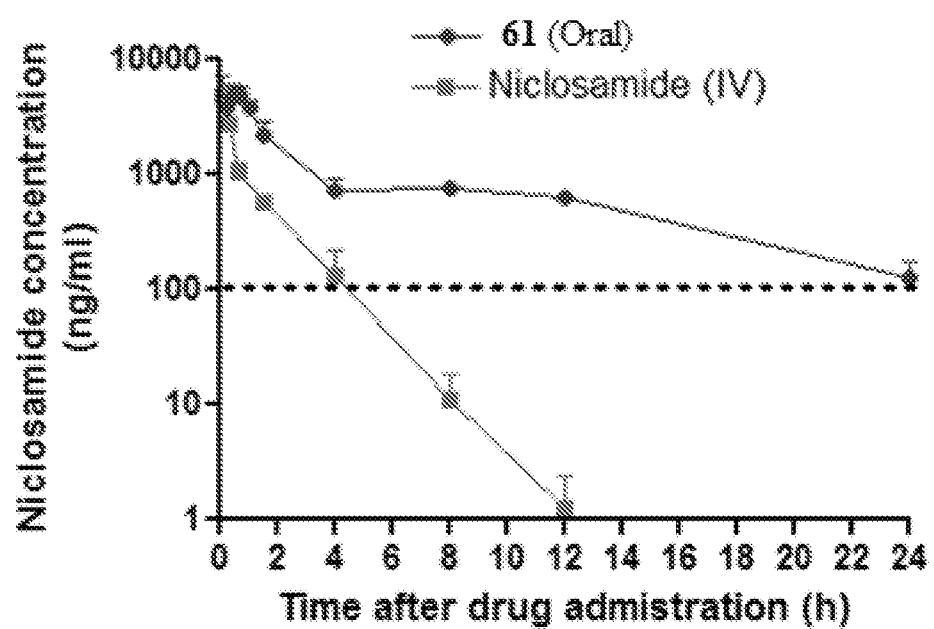
FIG. 7 is a graph depicting pharmacokinetic data for niclosamide and an exemplary compound.
Figure 8:
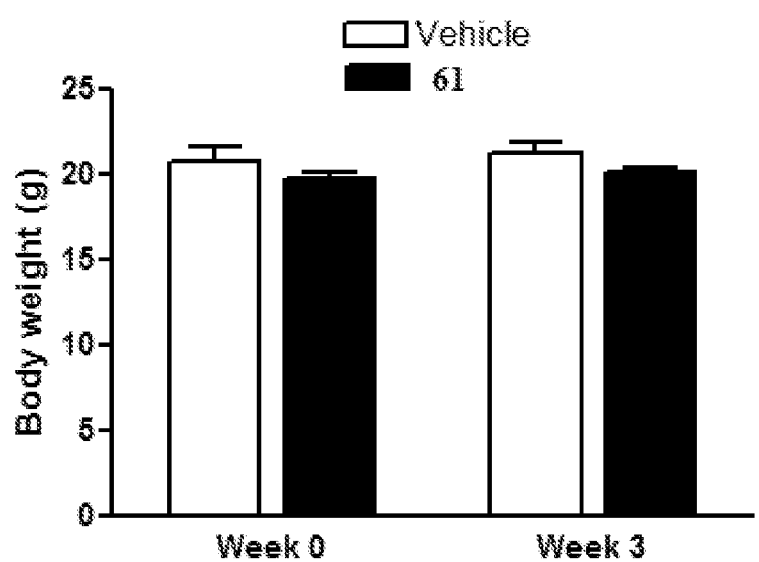
FIG. 8 is a graph illustrating 3-week tolerability for an exemplary compound.

In addition, compound 61 dosed orally at 200 mg/kg was well tolerated when administered daily to mice for three weeks, as judged by body weight and observing the behavior of the mice (FIG. 4).

Taken together, these experimental results demonstrate that SAR studies in the niclosamide chemotype have identified structural features that impact inhibition of Wnt/β-catenin signaling and plasma exposure when dosed orally. Through these studies, multiple active derivatives of niclosamide were identified, including compound 61, that, when dosed orally, metabolized to niclosamide and produced high concentrations of niclosamide in plasma and extended the duration of exposure to niclosamide. This discovery of niclosamide derivatives that improve systemic niclosamide drug exposure overcomes a significant barrier to the clinical translation of niclosamide to treat cancer. Moreover, it also allows the study of niclosamide in vivo in other diseases for which niclosamide has demonstrated biological activity. Thus, the findings described here may provide a breakthrough to a new class of niclosamide-based drug candidates to treat disease associated with its multi-function activity ranging from cancer to bacterial and viral disease, lupus and metabolic diseases such as type II diabetes, Non-Alcoholic Fatty Liver Disease (NAFLD), and Non-Alcoholic Steatohepatitis (NASH).

Example 13. Reduction of High Fat Diet (HFD)-Induced Hepatic Steatosis in Mice

Figure 9:
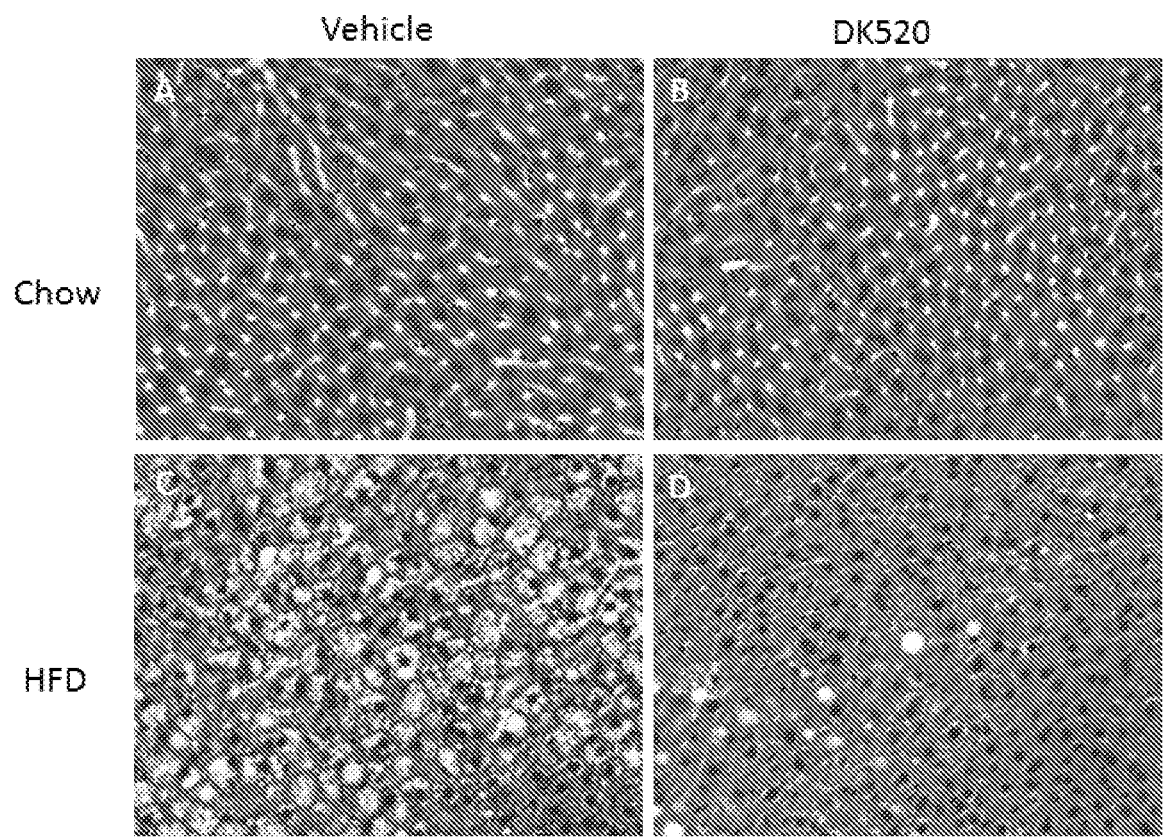
FIG. 9 is images of representative liver sections stained with H&E: A. Chow mice with vehicle; B. Chow mice with an exemplary compound; C. HFD mice with vehicle; D. HFD mice with an exemplary compound.

Five week old male C57BL/6J mice were fed with chow or high fat diet for two months, followed by same diet and oral gavage of vehicle (corn oil) or compound 61 at 200 mg/kg for three months (daily for 6 days a week from Monday to Saturday). Liver tissue samples were collected after the three month treatment. Pictures shown in FIG. 9 are representative liver sections stained with H&E. A. Chow mice with vehicle; B. Chow mice with compound 61; C. HFD mice with vehicle; D. HFD mice with compound 61. As can be seen, compound 61 had minimal to no effect on the liver of mice fed a normal chow diet. The white fat deposits look similar in both panel A and B. However, when mice were fed a high fat diet (panel C), a large amount of white fatty deposits can be seen along with a large amount of dysplastic liver tissue. Treatment of mice fed a high fat diet with compound 61 resulted in limited white fatty deposits without the dysplastic tissue architecture (panel D).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound selected from the group consisting of:
   4-chloro-2-((2-chloro-4-nitrophenyl)carbamoyl)phenyl octanoate;
   4-chloro-2-((2-chloro-4-nitrophenyl)carbamoyl)phenyl oleate;
   4-chloro-2-((2-chloro-4-nitrophenyl)carbamoyl)phenyl (9Z,12Z)-octadeca-9,12-dienoate; and 4-chloro-2-((2-chloro-4-nitrophenyl)carbamoyl)phenyl stearate, or a pharmaceutically acceptable salt thereof.

2. A pharmaceutical composition comprising at least one pharmaceutically acceptable carrier and an effective amount of a compound of claim 1, or a pharmaceutically acceptable salt thereof.

* * * * *